United States Patent [19]

Glazer

[11] Patent Number: 4,920,224

[45] Date of Patent: Apr. 24, 1990

[54] QUINAZOLIN-4(3H)-ONE DERIVATIVES AS ANTICOCCIDIAL AGENTS

[75] Inventor: Edward A. Glazer, Waterford, Conn.

[73] Assignee: Pfizer Inc., New York, N.Y.

[21] Appl. No.: 322,736

[22] Filed: Mar. 13, 1989

Related U.S. Application Data

[62] Division of Ser. No. 173,207, Mar. 24, 1988, Pat. No. 4,849,518, which is a division of Ser. No. 67,766, Jun. 22, 1987, Pat. No. 4,762,838.

[51] Int. Cl.$^5$ ............................................. C07D 401/12
[52] U.S. Cl. .................................... 544/284; 544/285; 544/287; 544/288; 544/289; 546/298; 560/17
[58] Field of Search .................... 544/284, 287, 288

[56] References Cited

U.S. PATENT DOCUMENTS

| Re. 26,833 | 3/1970 | Waletzky et al. | 514/259 |
|---|---|---|---|
| 2,625,549 | 1/1953 | Baker et al. | 544/287 |
| 2,651,632 | 9/1953 | Baker et al. | 544/287 |
| 2,694,711 | 11/1954 | Baker et al. | 544/287 |
| 2,796,417 | 6/1957 | Baker et al. | 544/287 |
| 2,811,524 | 10/1957 | Baker et al. | 544/284 |
| 3,047,462 | 7/1962 | Maillard et al. | 544/287 |
| 3,282,979 | 11/1966 | Reifschneider et al. | 560/18 |
| 3,674,857 | 7/1972 | Reifschneider | 560/18 |
| 3,748,327 | 7/1973 | Beyerle et al. | 544/289 |
| 4,252,947 | 2/1981 | Jolly et al. | 544/281 |
| 4,338,257 | 7/1982 | Patel | 560/18 |
| 4,340,596 | 7/1982 | Schein | 544/287 |
| 4,632,926 | 12/1986 | Giarda et al. | 544/287 |

FOREIGN PATENT DOCUMENTS

| 549233 | 11/1957 | Canada | 544/287 |
|---|---|---|---|
| 0098589 | 1/1984 | European Pat. Off. | |

OTHER PUBLICATIONS

The Merck Index, 10th Edition, monograph No. 3881 (Febrifugine), No. 4479 (Halofuginone).

*Primary Examiner*—Glennon H. Hollrah
*Assistant Examiner*—James H. Turnipseed
*Attorney, Agent, or Firm*—Peter C. Richardson; J. Trevor Lumb; Robert K. Blackwood

[57] ABSTRACT

Variously substituted trans-3-[3-(3-hydroxypiperid-2-yl)-2-oxopropyl]quinazolin-4(3H)-ones, a method of controlling or preventing coccidiosis in poultry therewith, intermediates therefor, and a process for the preparation of certain intermediates therefor.

1 Claim, No Drawings

QUINAZOLIN-4(3H)-ONE DERIVATIVES AS ANTICOCCIDIAL AGENTS

This is a division of application Ser. No. 07/173,207, filed on Mar. 24, 1988, now U.S. Pat. No. 4,849,518, which is a division of application Ser. No. 07/067,766, on filed June 22, 1987, now U.S. Pat. No. 4,762,838 with priority claimed under 35 USC 120 to PCT application PCT/US85/01685, filed on Aug. 30, 1985.

BACKGROUND OF THE INVENTION

The present invention is concerned with certain trans-3-[3-(3-hydroxy-2-piperidyl)-2-oxopropyl]-quinazolin-4-(3H)-one derivatives, a method of using same as anticoccidial agents, intermediates therefor, and a process for certain intermediates therefor.

Coccidiosis, a poultry disease, is caused by several species of protozoan parasites of the genus Eimeria, such as *E. acervulina* and *E. tenella*. In particular, *E. tenella* is the causative agent of a severe and often fatal infection of the ceca of chickens which is manifested by extensive hemorrhage, accumulation of blood in the cecum (a pouch between the large and small intestines) and the passage of blood in the droppings. Essentially, coccidiosis is an intestinal disease which is disseminated by birds picking up the infectious organism in droppings on contaminated litter or ground. By damaging the intestinal wall, the host animal is unable to utilize its food, goes off its feed, and in untreated cases the disease terminates in either the death of the animal or the survival of unthrifty birds known commonly as "culls."

Several classes of compounds have been reported to be useful as anticoccidial agents. Among these are various 6-azauracil derivatives (Miller, U.S. Pat. No. 4,239,888; summarizing several additional classes); trans-3-[3-(3-hydroxy-2-piperidyl)-2-oxopropyl]-4(3H)-quinazolinone (febrifugine; The Merck Index, Tenth Edition, monograph No. 3881); and trans-7-bromo-6-chloro-3-[3-(3-hydroxy-2-piperidyl)-2-oxopropyl]-4-(3H)-quinazolinone (halofuginone; The Merck Index, Tenth Edition, monograph No. 4479). Such anticoccidial compounds are more broadly defined by Waletzky et al., U.S. Pat. No. 3,320,124 (Re. 26,833); and Jolly et al., U.S. Pat. No. 4,252,947. European patent application 98589 broadly discloses structurally related hydrazine derivatives of trans-3-[3-(3-hydroxy-2-piperidyl)-2-oxopropyl]quinazolin-4(3H)-ones as anticoccidial agents.

Structurally related compounds are also reported to be useful in combatting theileriosis in cattle (Schein, U.S. Pat. No. 4,340,596). Although not in any manner specifically disclosed, the broad genus of Schein can be selectively chosen so as to define instant 6-trifluoromethyl-3-[3-(3-hydroxypiperid-2-yl)-2-oxopropyl]quinazolin-4(3H)-one. The present anticoccidial activity of the novel species is most surprising in view of the fact that the isomeric 7-trifluoromethyl analog (also defined by Schein's broad genus) is lacking in instant anticoccidial activity.

Structurally related compounds, including broad generic disclosure of 3-[3-(3-hydroxy-2-piperidyl)-2-oxopropyl]quinazolin-4(3H)-ones substituted on the aromatic ring with halogen, trifluoromethyl, lower alkylthio, methoxy, phenoxy, and benzyloxy groups, have also been disclosed as antimalarial agents by Baker et al., U.S. Pat. No. 2,694,711; see also Baker et al., U.S. Pat. Nos. 2,651,632 and 2,796,417 for compounds related to present intermediates. Although not in any manner specifically disclosed, a number of the instantly claimed compounds can be defined by said genera, once having knowledge of the present invention. While Baker et al. ('711) specifically disclose the 5-trifluoromethyl analog (isomeric with the present 6-trifluoromethyl analog), it is noteworthy that that compound is lacking in present anticoccidial activity.

SUMMARY OF THE INVENTION

Although above febrifugine and halofuginone are useful as anticoccidial agents, we have determined that a number of related compounds (for example, trans-3-[3-(3-hydroxy-2-piperidyl)-2-oxopropyl]quinazolin-4-(3H)-ones substituted on the aromatic ring as follows:
  6-phenoxy-7-chloro,
  6-(4-hydroxphenoxy)-7-chloro,
  7-(4-bromophenoxy),
  7-(4-bromophenoxy)-6-chloro,
  5-methylthio,
  6-(4-fluorobenzylthio)-7-chloro,
  7-cyano,
  5-trifluoromethyl,
  7-trifluoromethyl, or
  8-trifluoromethyl)
are lacking in useful anticoccidial activity in poultry. In spite of such lack of activity, we have surprisingly discovered a number of compounds, very closely related in structure, which are highly active as anticoccidial agents, as determined by their activity against *E. tenella*.

Thus the present invention is directed to anticoccidial compounds having the formula

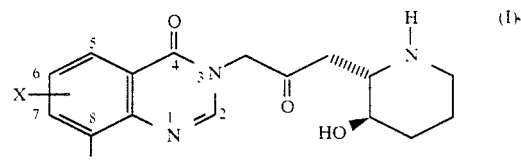

or

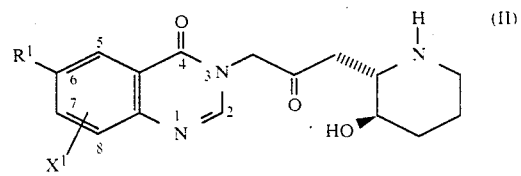

wherein
  X is fluoro, chloro, bromo or iodo substituted at the 6- or 7-position;
  R is $(C_1-C_4)$alkylthio;
  $X^1$ is hydrogen or fluoro, chloro, bromo, iodo or methoxy substituted either at the 7- or at the 8-position; and
  $R^1$ is cyano, trifluoromethyl, $(C_1-C_4)$alkylthio, 4-picolythio, 3,5-dichlorophenoxy,

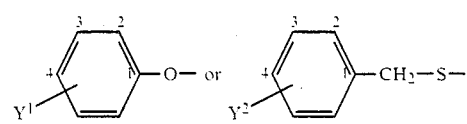

where $Y^1$ is hydrogen, fluoro, chloro, bromo or phenoxy; and $Y^2$ is chloro or bromo; with the proviso that $Y^1$ is other than hydrogen when $X^1$ is other than hydrogen, or a pharmaceutically-acceptable acid addition salt thereof.

The compounds of the present invention are racemic (not optically active). The heavy and dotted bonds in the various formulae therefore indicate relative, not absolute, stereochemistry.

Pharmaceutically-acceptable acid addition salts include, but are not restricted to, those with HCl, HBr, $H_2SO_4$, $CH_3SO_3H$, p—$CH_3C_6H_4SO_3H$, lactic acid, fumaric acid, citric acid and the like.

Most preferred compounds, because of their ease of preparation and high activity, are of the formula (I), particularly those compounds wherein $R^1$ is methylthio and $X^1$ is hydrogen, 7-fluoro, 7-chloro or 7bromo.

The present invention also encompasses a method of controlling or preventing coccidiosis in poultry which comprises administering to said poultry an anticoccidially effective amount of a compound of the formula (I) in drinking water or in nutritionally-balanced feed.

Also claimed are valuable intermediates of the formula:

(A) [structure III]

or

[structure IV]

wherein
X, R, $X^1$ and $R^1$ are as defined above;
$R^2$ is hydrogen, acetyl or ($C_1$-$C_4$)alkyl; and
$R^3$ is hydrogen or $COOR^4$; where R is allyl or ($C_1$-$C_4$)alkyl;
with the provisos that at least one of $R^2$ and $R^3$ is other than hydrogen, and that $R^3$ is hydrogen when $R^2$ is acetyl; and (B) [structure V]

or

[structure VI]

wherein
X, R, $X^1$ and $R^1$ are as defined above.

In addition, we claim a process for preparing a compound of the formula

[structure VII]

or

[structure VIII]

wherein
R is ($C_1$-$C_4$)alkylthio;
$R^5$ and $R^6$ are each independently ($C_1$-$C_4$)alkyl;
X is fluoro, chloro, bromo or iodo;
$R^7$ is ($C_1$-$C_4$)alkyl, 4-picolyl or

[structure]

$Y^2$ is chloro or bromo; and
$X^3$ is fluoro, chloro, bromo or iodo substituted at the 3- or 4-position; which comprises:
(a) reaction of a compound of the formula

[structure]

or

[structure]

with at least 2 molar equivalents of $NH_4SCN$ in the presence of substantially 1 molar equivalent of $Br_2$ in a reaction inert solvent comprising a ($C_1$-$C_4$)alkanoic acid;

(b) solvolyzing the resulting compound having the formula

[structure]

or

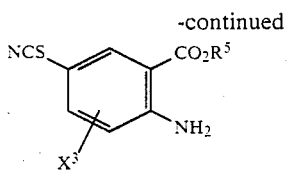

with a least one equivalent of a nucleophile in a reaction inert solvent comprising water or a $(C_1-C_4)$-alkanol; and (c) reacting the resulting thiophenoxide, having the formula

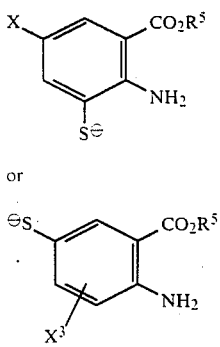

with a compound of the formula $$R^6X^4$$

or $$R^7X^4$$

wherein $X^4$ is a nucleophilically displaceable group, in the same or another reaction inert solvent to form a compound of the formula (VII) or (VIII).

The preferred nucleophile is an alkali metal alkoxide, particularly methoxide. The preferred solvent comprises methanol.

DETAILED DESCRIPTION OF THE INVENTION

The compounds of the present invention are readily prepared by nucleophilic displacement:

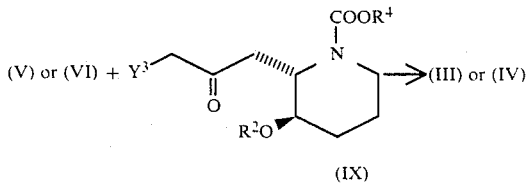

where in (III), (IV) and (IX), $R^2$ and $R^4$ are both defined as above but $R^2$ is other than hydrogen, and $Y^3$ is a nuycleophilically displaceable group such as chloro, bromo, iodo or mesylate; followed by solvolytic or hydrolytic removal of the groups $R^2$ and $COOR^4$. Because of their ready availability, preferred compounds of the formula (IX) have $Y^3$ as bromo, $R^2$ as methyl and $R^4$ as methyl or allyl.

The nucleophilic displacement reaction between compounds of the formulae (V) or (VI) and (IX) in all cases involves replacement of the leaving group, $Y^3$, with a relatively non-nucleophilic nitrogen. For this reason it is essential to employ a base of sufficient strength to form the anion of the compound (V) or (VI) in an amount at least sufficient to neutralize all of the acid ($HY^3$) coproduced in the reaction. Alkali metal $(C_1-C_4)$alkoxides are well suited for this purpose. The reaction is generally carried out in a reaction inert solvent such as a lower alkanol, acetonitrile or dimethylformamide. The solvent should be less acidic than the compound (V) or (VI), so as to facilitate formation of the required anion. Sodium methoxide as base in methanol as solvent represent conditions particularly well suited for the present reaction. The temperature employed for this reaction is best kept below 40° C. (e.g., temperatures in the range of 0°-30° C. are fully satisfactory). It should be high enough to provide a reasonable rate, but not so high as to lead to undue decomposition. As is well known in the art, rate will vary with the nature of the leaving group (e.g. rate: I>Br>Cl), the specific structure of the compound (V) or (VI), the concentration of reagents and the solvent. The reaction time should be such that the reaction is nearly complete [e.g. >95% conversion when equivalent amounts of the compounds (V) or (VI) and (IX) are employed] to maximize yields [e.g. reaction times 1 hour to several hours at ambient temperature are well suited when $Y^3$ is bromo, the base is sodium methoxide, the solvent is methanol, and the concentration of compound (IX) is in the range 3-10% (w/v)]. Of course, complete reaction can be facilitated by use of an excess of one of the reagents, e.g. an excess of the compound (V) or (VI) when it is the more readily available of the two reagents.

The present nucleophilic displacement reactions produce compounds of the above formula (III) or (IV) wherein $R^2$ is $(C_1-C_4)$alkyl and $R^3$ is $COOR^4$ (where $R^4$ is defined above). The groups $R^2$ and $COOR^4$ are readily removed, stepwise or in a single step, to produce the desired compounds of the formula (I) or (II). Thus the $(C_1-C_4)$alkyl ether group is conveniently and selectively removed by the action of $BBr_3$ in a reaction inert solvent at a temperature ranging from $-70°$ to $0°$ C. Methylene chloride as solvent is particularly well suited for this purpose, since solutions of $BBr_3$ therein are commercially available. This method produces intermediate compounds of the formula (III) or (IV) wherein $R^2$ is hydrogen. The $COOR^4$ group is then conveniently removed from the latter intermediates by briefly heating with concentrated aqueous HBr, e.g. heating in 48% HBr for 2 to 10 minutes at 80°-150° C.; heating in 6N HCl at or near reflux temperature; or concentrated HBr in glacial acetic acid at 0°-30° C. The latter process generally produces the compound (III) or (IV) wherein $R^3$ is hydrogen and $R^2$ is generally acetyl. The latter is removed by mild hydrolysis, e.g., 6N HCl at 10°-30° C.

Alternatively, the groups $R^2$ and $R^3$ are removed in reverse order, using 33% HBr in acetic acid at 10°-30° C. to remove the group $R^3$, followed by heating at or near reflux in 48% aqueous HBr to remove the group $R^2$; or both groups $R^2$ and $R^3$ are concurrently removed by use of the latter 48% HBr conditions.

The acid addition salts of the compounds of the present invention, if not directly isolated, for example, as the hydrobromide salt directly from the reaction mixture, are obtained by contacting the free base with at least one equivalent of the appropriate acid in a reaction inert solvent. Those salts which do not precipitate directly are isolated by concentration and/or the addition of a non-solvent. Conversely, the free base form is conveniently formed from an acid addition salt by neutralization of the latter in water with recovery of the free base by filtration or extraction into a water immiscible organic solvent.

The required starting compounds of the formula (V) or (VI) are generally prepared by methods known in the chemical art. Some of the required starting 2-aminobenzoic acids or esters required in the synthesis of the compounds (V) and (VI) are known, or accessible by known methods. Others, in particular those of the above formula (VII) or (VIII) are now more practically accessible via the presently discovered, improved process for their preparation, as summarized above and as detailed in specific preparations below.

The cocciodiostatic activity of the compounds of the present invention is demonstrated as follows. Groups of chicks (e.g. groups of five ten-day old SPF white Leghorn cockerels) are fed a nutritionally complete basal ration into which the test compound is incorporated at various concentrations. The basal ration is generally a commercial chick starter (e.g. Agway Commercial Chick Starter, available from the Agway Feed Co., Franklin, Connecticut), and is presented ad libitum to the chicks 24 hours before infection and continuously thereafter throughout the course of the tests.

Twenty-four hours after initiation of the medication the chicks are inoculated orally with 100,000 sporulated oocysts (*Eimeria tenella*) and the average weight per bird per group determined. In addition, a group of six chicks is fed the basal ration which contains none of the test compound (infected, untreated controls). A further group of six chicks serves as uninfected, untreated controls. The chicks are examined on the fifth and sixth day post-infection for signs of hemorrhage. On the sixth day post-infection, the average body weight per bird per group is determined, the birds necropsied, the cecum examined macroscopically, and a pathology index (average degree of infection [A.D.I.]) determined. Chicks which die prior to the fifth day post-infection are considered as toxic deaths. Those which die five days post-infection or later are considered as deaths due to disease. The degree of pathologic involvement at necropsy is expressed as the average degree based on the following scheme: 0=no cecal lesions; 1=slight lesions; 2=moderate lesions; 3=severe lesions; 4=death.

The efficacy of the test compound, at a given level in feed, is judged by comparison of the pathologic index with that of the unmedicated infected controls, expressed as the ratio:

$$\frac{A.D.I. \text{ (treated group)}}{A.D.I. \text{ (infected, untreated controls)}}$$

Against *E. tenella*, the compounds of the present invention generally show a value of said ratio no higher than 0.6 at a feed concentration no higher than 25 p.p.m. The typical range of results obtained with the compounds of the present invention are illustrated as follows:

| Compound | | | Ratios at Feed Concentration (ppm) | | | |
|---|---|---|---|---|---|---|
| (I)/(II) | $X/X^1$ | $R/R^1$ | 25 | 12.5 | 6.25 | 3.12 |
| (II) | 7-Cl | 6-(4-FC$_6$H$_5$O) | 0.0 | 0.0 | 0.33 | 0.67 |
| (I) | 6-Cl | 8-SCH$_3$ | 0.0 | 0.32 | 0.73 | 0.95 |
| (II) | 7-Br | 6-SC$_2$H$_5$ | 0.10 | 0.33 | 1.0 | 1.0 |
| (II) | H | 6-(3,5-Cl$_2$C$_6$H$_3$O) | 0.10 | 0.95 | 1.27 | 1.05 |

It will be noted that a ratio of 0.0 indicates 100% control of pathology due to the infection at the indicated feed concentration.

The compounds of this invention are orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate (such as aqueous solution of a water soluble salt) or added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals (for example, soybean oil meal, linseed oil meal, corncob meal), and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements may be added directly to the poultry feed to produce a nutritionally balanced, finished feed containing a therapeutically effective level of one or more of the compounds of this invention. The mixtures are thoroughly blended by standard procedures, such as in a twin shell blender, to ensure homogeneity.

It will, of course, be obvious to those skilled in the art that the use levels of the compounds described herein will vary under different circumstances. Continuous low-level medication, during the growing period; that is, during the first 6 to 12 weeks for chickens, is an effective prophylatic measure. In the treatment of established infections, higher levels may be necessary to overcome the infection. The use level in feed will generally be in the range of 3 to 100 ppm. When administered in drinking water, the level which will be that which will provide the same daily dose of medication, i.e. 3 to 100 ppm, factored by the weight ratio of the average daily consumption of feed to the average daily consumption of water.

The present invention is illustrated by the following examples. However, it should be understood that the invention is not limited to the specific details of these examples.

EXAMPLE 1

Allyl trans-2-[3-(7-chloro-6-(4-chlorophenoxy)-quinazolin-4(3H)-on-3-yl)-2-oxopropyl]-3-methoxypiperidine-1-carboxylate

[Formula (IV) with $X^1$=7-chloro, $R^1$=4-chlorophenoxy, $R^2$=methyl and $R^4$=allyloxycarbonyl]

Under a nitrogen atmosphere in a flame-dried flask at room temperature and with magnetic stirring, 0.921 g (0.003 mol) of 7-chloro-6-(4-chlorophenoxy)quinazolin-4(3H)-one was slurried in 3.0 ml of 1.1N sodium methoxide. After 15 minutes, 1.00 g (0.003 mol) of allyl trans-2-(3-bromo-2-oxopropyl)-3-methoxy-1-piperidinecarboxylate in 10 ml of methanol was added dropwise. After 2 hours, the reaction mixture was evaporated under reduced pressure, and the residue treated with water. The aqueous solution was extracted three times with 75 ml of dichloromethane. The combined extracts were dried over anhydrous magnesium sulfate, filtered, and evaporated to afford the title compound: yield 1.28 g (76%); m.p. 138°–141° C. H-NMR(CDCl$_3$); 1.3 to 1.9 (m, 4H), 2.6–3.4 (m, 6H), 3.3 (s, 3H), 4.9 (s, 2H), 4.5–6.2 (m, 5H), 7.1 (q, 4H), 7.6 (s, 1H), 7.8 (d, 2H) ppm.

By the same method, other suitably substituted 6-phenoxyquinazolin-4(3H)-ones were converted to allyl trans-2-[3-(7-$X^1$ substituted)-6-($Y^1$ substituted phenoxy)-quinazolin-4(3H)-on-3-yl)-2-oxopropyl]-3-methoxypiperidine-1-carboxylates as follows:

| $Y^1$ | $X^1$ | m.p.(°C.) | yield(%) |
|---|---|---|---|
| H | H | 122–125 | 43 |
| 4-Br | H | 88–170 | 57 |
| 4-Cl | H | foam$^{(a)}$ | 76 |
| 3-Cl | H | oil$^{(b)}$ | 83 |
| 2-Cl | H | foam$^{(b)}$ | 89 |
| 3,5-di-Cl | H | foam$^{(b)}$ | 47 |
| 4-OPh | H | 110–152 | 66 |
| 4-Br | Cl | 142–144 | 82 |
| 4-Cl | Cl | 138–141 | 76 |
| 4-F | Cl | (b) | 54 |
| 4-Cl | Br | 145–148 | 67 |
| 3-Cl | Cl | foam$^{(b)}$ | 62 |
| 3-Br | Cl | (b) | 67 |

$^{(a)}$H-NMR(CDCl$_3$)delta: 1.4–2.0 (m, 4 H), 2.6–3.6 (m, 6 H), 3.3 (s, 3 H), 5.2 (s, 2 H), 4.5–6.2 (m, 5 H), 6.9–7.9 (m, 8 H) ppm;
$^{(b)}$H-NMR(CDCl$_3$), like that of the 4-chlorophenoxy analog, is consistent with the assigned structure.

EXAMPLE 2 trans-7-Chloro-6-(4-chlorophenoxy)-3-[3-(3-methoxypiperid-2-yl)-2-oxopropyl]-quinazolin-4(3H)-one Dihydrobromide

[Compound (IV) with $X^1$=chloro, $R^1$=4-chlorophenoxy, $R^2$=methyl and $R^3$=hydrogen]

A solution of 1.15 g (0.002 mol) of the title product of the preceding Example in 50 ml of 33% hydrobromic acid in acetic acid was stirred at room temperature for 45 minutes. The solvent was evaporated under reduced pressure and the residue triturated with ethanol. The resulting suspension was filtered to afford the present title compound as a white solid: m.p. 229°–231° C.; yield 0.897 g (68%).

By the same method, the other compounds of the preceding Example were converted to the corresponding dihydrobromide salts of trans-7-($X^1$ substituted)-6-($Y^1$-substituted phenoxy)-3-[3-(3-methoxypiperidin-2-yl)-2-oxopropyl]quinazolin-4(3H)-ones as follows:

| $Y^1$ | $X^1$ | m.p.(°C.) | yield(%) |
|---|---|---|---|
| H | H | 215–218 | 62 |
| 4-Br | H | 218–220 | 35 |
| 4-Cl | H | —* | 26 |
| 3-Cl | H | 212–219 | 42 |
| 2-Cl | H | 233–235 | 57 |
| 3,5-di-Cl | H | 240–243 | 59 |
| 4-OPh | H | 225–227 | 82 |
| 4-Br | Cl | 224–227 | 65 |
| 4-Cl | Cl | 229–231 | 68 |
| 4-F | Cl | 247–248 | 68 |
| 4-Cl | Br | 230–232 | 50 |
| 3-Cl | Cl | 235–238 | 46 |
| 3-Br | Cl | 221–222 | 53 |

*$^1$H-NMR(DMSO-d$_6$)delta: 1.3–2.1 (m, 4 H), 2.9–3.6 (m, 6 H), 3.4 (s, 3 H), 5.2 (s, 2 H), 7.0–7.8 (m, 7 H), 8.4 (s, 1 H).

EXAMPLE 3 trans-7-Chloro-6-(4-chlorophenoxy)-3-[3-(3-hydroxypiperid-2-yl)-2-oxopropyl]-quinazolin-4(3H)-one Dihydrobromide

[Formula (II) with $X^1$=7-chloro and $R^1$=4-chlorophenoxy]

A solution of 0.80 g (0.0012 mol) of the title product from the preceding Example in 40 ml of 48% hydrobromic acid was heated at reflux for 15 minutes. The reaction mixture was cooled to room temperature and evaporated to an oil under reduced pressure. The residue was treated with several ml of ethanol and the resulting solution was evaporated. This operation was repeated several times. Finally, the residue was taken up in hot ethanol and the product crystallized upon cooling to room temperature. Filtration gave the title compound: m.p. 185°–188° C.; yield 0.674 g (86%).

Analysis calculated for $C_{22}H_{21}Cl_2N_3O_4 \cdot 2HBr \cdot \frac{1}{2}H_2O$: C, 41.73; H, 3.82; N, 6.64%. Found: C, 41.74; H, 3.80; N, 6.75%.

By the same method the other products of the preceding Example were converted to corresponding dihydrobromide salts of trans-7-($X^1$ substituted)-6-($Y^1$ substituted phenoxy-3-[3-(3-hydroxypiperid-2-yl)-2-oxopropylquinazolin-4(3H)-ones as follows:

| $Y^1$ | $X^1$ | m.p.(°C.) | yield(%) |
|---|---|---|---|
| H | H | 223–224 | 58 |
| 4-Br | H | 226–227 | 53 |
| 4-Cl | H | foam$^{(a)}$ | 35 |
| 3-Cl | H | 224–226 | 79 |
| 2-Cl | H | 238–239 | 85 |
| 3,5-di-Cl | H | foam$^{(b)}$ | 43 |
| 4-OPh | H | 237–239 | 69 |
| 4-Br | Cl | 186–187 | 94 |
| 4-Cl | Cl | 185–188 | 86 |
| 4-F | Cl | 239–240 | 52 |
| 4-Cl | Br | 238–239 | 88 |
| 3-Cl | Cl | 247–248 | 82 |
| 3-Br | Cl | 250–251 | 82 |

$^{(a)}$$^{13}$C-NMR(DMSO-d$_6$): 20.307, 30.817, 43.155, 54.537, 56.379, 66.768, 112.46, 121.185, 122.213, 126.232, 128.227, 129.336, 130.123, 143.252, 147.019, 154.575, 155.508, 159.215, 200.448.
$^{(b)}$$^1$H-NMR(DMSO-d$_6$): 1.5–2.1 (m, 4 H), 2.9–3.8 (m, 6 H), 5.2 (s, 2 H), 7.2–7.9 (m, 6 H), 8.4 (s, 1 H).

EXAMPLE 4

Allyl trans-2-[3-(7-Bromo-6-methylthioquinazolin-4(3H)-on-3-yl)-2-oxopropyl]-3-methoxy-1-piperidinecarboxylate Under a nitrogen atmosphere in a flame dried flask at room temperature and with magnetic stirring, a suspension of 0.43 g (0.00136 mol) of 7-bromo-6-methylthioquinazolin-4(3H)-one formic acid salt in 5 ml of methanol was treated with two equivalents of sodium methoxide in methanol (approximately 1N). After 15 minutes 0.53 g (0.0016 mol) of allyl trans-2-(3-bromo-2-oxopropyl)-3-methoxy-1-piperidinecarboxylate was added in one portion. After being stirred for an hour, the reaction mixture was evaporated under reduced pressure, and the residue was taken up in about 15 ml of water. The aqueous solution was extracted three times with 15 ml portions of dichloromethane. The combined extracts were dried over anhydrous sodium sulfate, filtered, and evaporated to afford the title compound: yield 0.61 g (86%). $^1$H—NMR(CDCl$_3$): 1.3–2.0 ppm (multiplet, 4H, CH$_3$OCHCH$_2$CH$_2$CH$_2$N), 2.6 (singlet, 3H, CH$_3$S), 2.8–3.0 (multiplet, 4H, COCH$_2$CH and NCH$_2$), 3.3 (broad singlet, 1H, CH$_2$CHNCO), 3.4 (singlet, 3H, CH$_3$O), 4.0 (broad doublet, 1H, CHOCH$_3$), 4.6 (broad doublet, 2H, CH$_2$CH=CH$_2$), 4.8–5.1 (multiple peaks, 2H, NCH$_2$CO), 5.2–5.4 (multiplet, 2H, CH$_2$=CH), 5.9 (octet, 1H, CH=CH$_2$), 7.3 (singlet, 1H, aromatic H), 7.9 (singlet, 1H, aromatic H), 7.95 (singlet, 1H, N=CH—N).

EXAMPLE 5 trans-7-Bromo-3-[3-(3-methoxypiperid-2-yl)-2-oxopropyl]-6-methylthioquinazolin-4(3H)-one Dihydrobromide A solution of 0.61 g (0.00116 mol) of the title product of the preceding Example and 30 ml of 33% hydrobromic acid in acetic acid was stirred at room temperature for 30 minutes. The solution was evaporated under reduced pressure and treated with a few ml of ethanol. The ethanolic solution was evaporated, and the residue was treated again with ethanol. Again the solution was evaporated. Ethanol was added a final time. After standing overnight at room temperature the solution afforded the present title compound as a cyrstalline material: m.p. 250°–253° C.; yield 0.11 g (16%); mass spectrum m/e 440 (molecular ion +1), 407 (−32, —CH$_3$OH), 137 (parent peak) amongst others.

EXAMPLE 6 trans-7-Bromo-3-[3-(3-hydroxypiperid-2-yl)-2-oxopropyl]-6-methylthio quinazolin-4(3H)-one Dihydrobromide In a 25 ml round bottom flask, a solution of 0.175 g (0.00029 mol) of the title product of the preceding Example and 10 ml of aqueous 48% hydrobromic acid was immersed in oil bath preheated to 150° C. Heating was continued for 15 minutes. After cooling to nearly room temperature, the reaction mixture was evaporated under reduced pressure. The residue was treated with a few ml of ethanol, and the resulting solution was evaporated. This operation was repeated. Finally the residue was taken up in 50 ml of hot ethanol, and filtered to remove some insoluble matter. The filtrate was concentrated to about 2 ml. Crystals formed and were filtered to give the instant title compound: yield 0.107 g (63%); high resolution mass spectrum m/e 425.0397 (molecular ion with isotope at 427.0416, theory 425.0408). $^1$H—NMR(DMSO-d$_6$) 1.4–2.0 ppm (multiplet, 4H, HOCHCH$_2$CH$_2$CH$_2$N), 2.6 (singlet, 3H, SCH$_3$), 2.8–3.0 (multiplet, 2H, NCH$_2$), 3.1–3.6 (multiplet, 4H, CH$_2$N, CHOH, CH$_2$CHN), 5.1 (singlet, 2H, NCH$_2$CO), 5.6 (doublet, 1H, OH), 7.8 (singlet, 1H, aromatic H), 8.0 (singlet, 1H, aromatic H), 8.2 (singlet, 1H, N=CH—N).

EXAMPLE 7

Allyl trans-2-[3-(7-Bromo-6-ethylthioquinazolin-4(3H)-on-3-yl)-2-oxopropyl]-3-methoxy-1-piperidinecarboxylate In the manner of Example 4, 0.743 g (0.00224 mol) of 7-bromo-6-ethylthioquinazolin-4(3H)-one formic acid salt and 0.750 g (0.00224 mol) of allyl trans-2-(3-bromo-2-oxopropyl)-3-methoxy-1-piperidinecarboxylate were converted into the title compound. After flash chromatography on silica gel (eluant 3% methanol in chloroform) there was obtained the pure product: yield 0.61 g (51%) mass spectrum m/e 537 (molecular ion with expected isotope pattern), 41 (parent peak, CH$_2$=CH—CH$_2$+) among others. $^1$H—NMR(CDCl$_3$) 1.4 ppm (triplet, 3H, SCH$_2$CH$_3$), 1.4–2.1 (multiplet, 4H, OCHCH$_2$CH$_2$CH$_2$N), 2.8–3.4 (multiplet, 6H, NCH$_2$, SCH$_2$CH$_3$, COCH$_2$CH), 3.4 (singlet, 3H, OCH$_3$), 4.0 (broad singlet, 1H, CHNCO), 4.6 (doublet, 2H, CH$_2$CH=CH$_2$), 5.0 (singlet, 2H, NCH$_2$CO), 5.0–5.5 (multiplet, 2H, CH=CH$_2$), 5.6–6.1 (octet, 1H, CH$_2$=CH), 7.3 (singlet, 1H, aromatic H), 7.9 (singlet, 2H, aromatic H, N=CH—N).

EXAMPLE 8 trans-7-Bromo-3-[3-(3-methoxypiperid-2-yl)-2-oxopropyl]-6-ethylthioquinzolin-4(3H)-one Dihydrobromide In the manner of Example 5, 0.61 g (0.00113 mol) of the title product of the preceding Example was transformed into present title compound: yield 0.316 g (45%); m.p. 225°–228° C.; mass spectrum m/e 454 (molecular ion+H with expected isotope pattern), 421 (−32, —CH$_3$OH), 137 (parent peak) among others. $^1$H—NMR(DMSO-d$_6$) 1.35 ppm (triplet, 3H, SCH$_2$CH$_3$), 1.4–2.2 (multiplet, 4H, OCHCH$_2$CH$_2$CH$_2$N), 2.9–3.1 (multiplet, 2H, CH$_2$N), 3.1–3.3 (multiplet, 5H, SCH$_2$CH$_3$, COCH$_2$CH) 3.3 (singlet, 3H, OCH$_3$), 3.6 (broad singlet, 1H, CH$_3$OCH), 5.1 (singlet, 2H, NCH$_2$CO), 7.9 (singlet, 1H, aromatic H), 8.0 (singlet, 1H, aromatic H), 8.2 (singlet, 1H, N=CH—N).

EXAMPLE 9 trans-7-Bromo-3-[3-(3-hydroxypiperid-2-yl)-2-oxopropyl]-6-ethylthioquinazolin-4(3H)-one Dihydrobromide In the manner of Example 6, 0.31 g (0.00058 mol) of title product of the preceding Example was converted to present title compound: yield 0.263 g (87%); mass spectrum m/e 439 (molecular ion with expected isotope pattern), 421 (−18, —H$_2$O), 137, 96, 82 (parent peak) among others. $^1$H—NMR(DMSO-d$_6$) 1.35 ppm (triplet, 3H, SCH$_2$CH$_3$), 1.4–2.0 (multiplet, 4H, OCHCH$_2$CH$_2$CH$_2$N), 2.8–3.0 (multiplet, 2H, NCH$_2$), 3.1–3.6 (multiplet, 6H, SCH$_2$CH$_3$, COCH$_2$CHCHO), 5.1 (singlet, 2H, NCH$_2$CO), 7.9 (singlet, 1H, aromatic H), 8.0 (singlet, 1H, aromatic H), 8.2 (singlet, 1H, N=CH—N).

EXAMPLE 10

Allyl trans-2-[3-(7-Fluoro-6-methylthioquinazolin-4(3H)-on-3-yl)-2-oxopropyl]-3-methoxy-1-piperidinecarboxylate In the manner of Example 4, 0.462 g (0.0018 mol) of 7-fluoro-6-methylthioquinazolin-4(3H)-one formic acid salt and 0.750 g (0.00224 mol) of allyl trans-2-(3-bromo-2-oxopropyl)-3-methoxy-1-piperidinecarboxylate were converted into the title compound: yield 0.50 g (60%). $^1$H—NMR(CDCl$_3$) 1.4–2.1 ppm (multiplet, 4H, OCHCH$_2$CH$_2$CH$_2$N), 2.6 (singlet, 3H, SCH$_3$), 2.8–3.4 (multiplet, 4H, NCH$_2$, COCH$_2$CH), 3.4 (singlet, 3H, OCH$_3$), 4.0 (broad singlet, 1H, CHNCO), 4.6 (doublet, 2H, CH$_2$CH=CH$_2$), 5.0 (singlet, 2H, NCH$_2$CO), 5.0–5.5 (multiplet, 2H, CH=CH$_2$), 5.6–6.1 (octet, 1H, CH$_2$=CH), 7.3 (doublet, 1H, aromatic H), 7.9 (singlet, 1H, N=CH—N), 8.0 (doublet, 1H, aromatic H).

EXAMPLE 11 trans-7Fluoro-3-[3-(3-methoxypiperid-2-yl)-2-oxopropyl]-6-methylthioquinazolin-4(3H)-one Dihydrobromide In the manner of Example 5, 0.48 g (0.001 mol) of the title product of the preceding Example was transformed into the instant title compound: yield 0.324 g (58%); m.p. 214°–216° C.

EXAMPLE 12 trans-7-Fluoro-3-[3-(3-hydroxypiperid-2-yl)-2-oxopropyl]-6-methylthioquinazolin-4(3H)-one Dihydrobromide In the manner of Example 6, 0.32 g (0.00059 mol) of the title product of the preceding Example was converted to present title compound: yield 0.188 g (60%); mass spectrum m/e 366 (molecular ion+H), 347 (−18, —H$_2$O), 137 (parent peak) among others. $^1$H—NMR(DMSO-d$_6$) 1.4–2.1 ppm (multiplet, 4H, OCHCH$_2$CH$_2$CH$_2$N), 2.6 (singlet, 3H, SCH$_3$), 2.8–3.0 (multiplet, 2H, NCH$_2$), 3.1–3.7 (multiplet, 4H, COCH$_2$CHCHO), 5.1 (singlet, 2H, NCH$_2$CO), 7.5 (doublet, 1H, aromatic H), 7.9 (doublet, 1H, aromatic H), 8.3 (singlet, 1H, N=CH—N), 8.9 (broad singlet, 2H, NH$_2$).

EXAMPLE 13

Allyl trans-2-[3-(7-Iodo-6-methylthioquinazolin-4(3H)-on-3-yl)-2-oxopropyl]-3-methoxy-1-piperidinecarboxylate In the manner of Example 4, 1.09 g (0.003 mol) of 7-iodo-6-methylthioquinazolin-4(3H)-one formic acid salt and 1.0 g (0.003 mol) of allyl trans-2-(3-bromo-2-oxopropyl)-3-methoxy-1-piperidinecarboxylate were converted into the title compound: yield 0.53 g (31%); mass spectrum m/e 571 (molecular ion), 539 (−32, —CH$_3$OH), 221 (parent peak). $^1$H—NMR(CDCl$_3$) 1.4–2.1 ppm (multiplet, 4H, OCHCH$_2$CH$_2$CH$_2$N), 2.6 (singlet, 3H, SCH$_3$), 2.8–3.4 (multiplet, 4H, NCH$_2$, COCH$_2$CH), 3.4 (singlet, 3H, OCH$_3$), 4.0 (broad singlet, 1H, CHNCO), 4.6 (doublet, 2H, CH$_2$CH=CH$_2$), 5.0 (singlet, 2H, NCH$_2$CO), 5.0–5.5 (multiplet, 2H, CH=CH$_2$), 5.6–6.1 (octet, 1H, CH$_2$=CH), 7.7 (singlet, 1H, aromatic H), 7.8 (singlet, 1H, N=CH—N), 8.2 (singlet, 1H, aromatic H).

EXAMPLE 14 trans-7-Iodo-3-[3-(3-methoxypiperid-2-yl)-2-oxopropyl]-6-methylthioquinazolin-4(3H)-one Dihydrobromide In the manner of Example 5, 0.53 g (0.00093 mol) of the title product of the preceding Example was transformed into instant title compound: yield 0.264 g (44%); m.p. 210°–230° C.; mass spectrum m/e 488 (molecular ion+H+), 469 (−18, —H$_2$O?), 455 (−32, —CH$_3$OH), 137 (parent peak among others. $^1$H—NMR(DMSO-d$_6$) 1.2–2.0 ppm (multiplet, 4H, OCHCH$_2$CH$_2$CH$_2$N), 2.6 (singlet, 3H, SCH$_3$), 2.8–3.0 (multiplet, 2H, NCH$_2$), 3.1–3.7 (multiplet, 4H, COCH$_2$CHCHO), 3.3 (singlet, 3H, OCH$_3$), 5.1 (singlet, 2H, NCH$_2$CO), 7.7 (singlet, 1H, aromatic H), 8.2 (singlet, 1H, aromatic H), 8.25 (singlet, 1H, N=CH—N), 8.7 (broad singlet, 2H, NH$_2$).

EXAMPLE 15 trans-7-Iodo-3-[3-(3-hydroxypiperid-2-yl)-2-oxopropyl]-6-methylthioquinazolin-4(3H)-one Dihydrobromide In the manner of Example 6, 0.262 g (0.0004 mol) of title product of the preceding Example was converted to the title compound: yield 0.234 g (91%); mass spectrum m/e 473 (molecular ion), 455 (−18, —H$_2$O), 318 (parent peak) among others. $^1$H—NMR(DMSO-d$_6$) 1.2–2.0 ppm (multiplet, 4H, OCHCH$_2$CH$_2$CH$_2$N), 2.6 (singlet, 3H, SCH$_3$), 2.8–3.0 (multiplet, 2H, NCH$_2$), 3.1–3.6 (multiplet, 4H, COCH$_2$CHCHO), 5.1 (singlet, 2H, NCH$_2$CO), 7.7 (singlet, 1H, aromatic H), 8.2 (singlet, 1H, aromatic H), 8.25 (singlet, 1H, N=CH—N), 8.7 (broad singlet, 2H, NH$_2$).

EXAMPLE 16

Allyl trans-2-[3-(6-Chloro-7-methylthioquinazolin-4(3H)-on-3-yl)-2-oxopropyl]-3-methoxy-1-piperidinecarboxylate In the manner of Example 4, 0.679 g (0.003 mol) of 6-chloro-7-methylthioquinazolin-4(3H)-one and 1.0 g (0.003 mol) of allyl trans-2-(3-bromo-2-oxopropyl)-3-methoxy-1-piperidinecarboxylate were converted into the title compound: yield 0.56 g (39%). $^1$H—NMR(CDCl$_3$) 1.4–2.2 ppm (multiplet, 4H, OCHCH$_2$CH$_2$CH$_2$N), 2.6 (singlet, 3H, SCH$_3$), 2.8–3.4 (multiplet, 4H, NCH$_2$, COCH$_2$CH), 3.4 (singlet, 3H, OCH$_3$), 4.0 (broad singlet, 1H, CHNCO), 4.6 (doublet, 2H, CH$_2$CH=CH$_2$), 5.0 (singlet, 2H, NCH$_2$CO), 5.0–5.5 (multiplet, 2H, CH=CH$_2$), 5.6–6.1 (octet, 1H, CH$_2$=CH), 7.4 (singlet, 1H, aromatic H), 7.9 (singlet, 1H, N=CH—N), 8.2 (singlet, 1H, aromatic H).

EXAMPLE 17 trans-6-Chloro-3-[3-(3-methoxypiperid-2-yl)-2-oxopropyl]-7-methylthioquinazolin-4(3H)-one Dihydrobromide In the manner of Example 5, 0.56 g (0.00118 mol) of title product of the preceding Example was transformed into the present title compound: yield 0.27 g (41%); m.p. 225°–255° C.; mass spectrum m/e 396 (molecular ion+H+), 363 (−32, —CH$_3$OH), 137 (parent peak) among others; $^1$H—NMR(DMSO-d$_6$) 1.4–1.9 ppm (multiplet, 4H, OCHCH$_2$CH$_2$CH$_2$N), 2.6 (singlet, 3H, SCH$_3$), 2.8–3.0 (multiplet, 2H, NCH$_2$), 3.1–3.7 (multiplet, 4H, COCH$_2$CHCHO), 3.3 (singlet, 3H, OCH$_3$), 5.1 (singlet, 2H, NCH$_2$CO), 7.5 (singlet, 1H, aromatic H), 8.1 (singlet, 1H, aromatic H), 8.25 (singlet, 1H, N=CH—N), 8.7 (broad singlet, 2H, NH₂).

EXAMPLE 18 trans-6-Chloro-3-[3-(3-hydroxypiperid-2-yl)-2-oxo-propyl]-7-methylthioquinazolin-4(3H)-one Dihydrobromide In the manner of Example 6, 0.26 g (0.000546 mol) of title product of the preceding Example was converted to the instant title compound: yield 0.104 g (35%); high resolution mass spectrum m/e 363.0835 (molecular ion −18, —H₂O); ¹H—NMR(DMSO-d₆) 1.4–2.0 ppm (multiplet, 4H, OCHCH₂CH₂CH₂N), 2.6 (singlet, 3H, SCH₃), 2.8–3.0 (multiplet, 2H, NCH₂), 3.1–3.6 (multiplet, 4H, COCH₂CHCHO), 5.1 (singlet, 2H, NCH₂CO), 7.5 (singlet, 1H, aromatic H), 8.1 (singlet, 1H, aromatic H), 8.25 (singlet, 1H, N=CH—N), 8.7 (broad singlet, 2H, NH₂).

EXAMPLE 19

Allyl trans-2-[3-(6-Substituted- 7- or 8-substituted-quinazolin-4(3H)-on-3-yl)-3-methoxypiperidine-1-carboxylates By the method of Example 4, equivalent amounts of the appropriately substituted quinazolin-4(3H)-one and allyl trans-2-(3-bromo-2-oxopropyl)-3-methoxy-1-piperidine-1-carboxylate were converted to the following title products substituted as follows:

| 6-Substituent | 7- or 8-Substituent | Yield | m.p.(°C.) |
|---|---|---|---|
| methylthio | none | 79 | foam⁽ᵃ⁾ |
| ethylthio | none | 81 | oil⁽ᵇ⁾ |
| propylthio | none | 87 | oil⁽ᵇ⁾ |
| 4-bromobenzylthio | none | 68 | 119–121 |
| 4-chlorobenzylthio | 7-chloro | 49 | 85–92 |
| 4-bromobenzylthio | 7-chloro | 44 | foam⁽ᵇ⁾ |
| 4-picolylthio | 7-chloro | 42 | oil⁽ᵇ⁾ |
| methylthio | 7-methoxy | 53 | (c) |
| methylthio | 7-chloro | 81 | oil⁽ᵇ⁾ |
| ethylthio | 7-chloro | 78 | oil⁽ᵇ⁾ |
| propylthio | 7-chloro | 54 | (b) |
| methylthio | 7-bromo | 86 | (b) |
| methylthio | 7-fluoro | 60 | (b) |
| methylthio | 7-iodo | 31 | (b) |
| ethylthio | 7-bromo | 51 | (b) |
| methylthio | 8-chloro | 64 | oil⁽ᵇ⁾ |
| methylthio | 8-bromo | 48 | (b) |
| ethylthio | 8-chloro | 81 | (b) |
| ethylthio | 8-bromo | 86 | (b) |
| chloro | 8-methylthio | 55 | 128–133 |
| chloro | 7-methylthio | 39 | oil⁽ᵇ⁾ |

⁽ᵃ⁾¹H-NMR(CDCl₃): 1.4–2.1 (m, 4 H), 2.6 (s, 3 H), 2.8–3.6 (m, 6 H), 3.5 (s, 3 H), 4.6–6.3 (m, 5 H), 5.0 (s, 2 H), 7.6–8.1 (m, 4 H).
⁽ᵇ⁾¹H-NMR consistent with assigned structure, having key features as in footnote (a).
⁽ᶜ⁾tlc Rf 0.82 (9:1 CHCl₃:CH₃OH).

EXAMPLE 20

Allyl trans-2-[3-(7-Chloro-6-[4-bromobenzylthio]quinazolin-4(3H)-on-3-yl)-2-oxopropyl]-3-hydroxypiperidine-1-carboxylate A solution of 0.55 g (0.87 mmol) of the 6-(4-bromobenzylthio)-7-chloro product of the preceding Example in 20 ml of dichloromethane was cooled to −15° C. under argon. While stirring, 4.4 ml of 1.0M boron tribromide in dichloromethane was added dropwise by syringe. The reaction was stirred 30 minutes at −15° C., allowed to warm to 20° C., and stirred an additional 30 minutes. The solution was then poured into 50 ml of saturated aqueous sodium bicarbonate. The aqueous phase was extracted five times with 50 ml portions of dichloromethane. The extracts were combined with the organic layer, dried over anhydrous magnesium sulfate, and evaporated to yield the title compound as an oil: yield 0.511 g (95%). This material was used without further purification in the procedure of the next Example.

EXAMPLE 21 trans-7-Chloro-3-[3-(3-hydroxypiperid-2-yl)-2-oxo-propyl]-6-(4-bromobenzylthio)-quinazolin-4(3H)-one Dihydrochloride A suspension of 0.50 g (0.8 mmol) of the product from the preceding Example in 25 ml of 6N hydrochloric acid was heated at reflux for 30 minutes. The solvent was evaporated and the residue recrystallized from ethanol to afford the title compound as a solid: m.p. 190°–193° C.; yield 137 ml (28%).

EXAMPLE 22

Other Allyl trans-2-[3-(6-Substituted-7-Substituted-quinazolin-4(3H)-on-3-yl)-2-oxopropyl]-3-hydroxypiperidine-1-carboxylates By the method of Example 20, the appropriately substituted products of Example 19 were converted to title products substituted as follows:

| 6-Substituent | 7-Substituent | Yield | tlc Rf⁽ᵃ⁾ |
|---|---|---|---|
| 4-chlorobenzylthio | chloro | 67 | 0.71 |
| 4-picolylthio | chloro | 78 | 0.47 |
| methylthio | methoxy | 69 | 0.60 |

⁽ᵃ⁾eluant: 9:1 CHCl₃:CH₃OH

EXAMPLE 23 trans-7-Chloro-3-[3-(3-hydroxypiperid-2-yl)-2-oxo-propyl]-6-(4-picolythio)-quinazolin-4(3H)-one Dihydrochloride By the method of Example 21, the 6-(4-picolythio)-7-chloro intermediate of the preceding Example was converted to instant title product as a foam in 61% yield; tlc Rf 0.48 (10:2:1 CHCl₃:ethanol:conc. NH₄OH).

EXAMPLE 24 trans-7-Chloro-3-[3-(3-hydroxypiperid-2-yl)-2-oxo-propyl]-6-(4-chlorobenzylthio)-quinazolin-4(3H)-one Dihydrobromide Using the conditions of Example 3 (refluxing 48% HBr) the 6-(4-chlorobenzylthio)-7-chloro product of Example 22 was converted to the instant title product, m.p. 260°–263° C., in 47% yield.

EXAMPLE 25 trans-7-Methoxy-3-[3-(3-hydroxypiperid-2-yl)-2-oxo-propyl]-6-methylthioquinazolin-4(3H)-one Dihydrobromide By heating in 48% HBr at 100° C. for 12 minutes, the 6-methylthio-7-methoxy product of Example 22 was converted to the instant title product, isolated in 69% yield as a foam having ¹H—NMR(DMSO-d₆) 1.4–2.3 (m, 4H), 2.5 (s, 3H), 2.9–3.8 (m, 6H), 4.0 (s, 3H), 5.2 (s, 2H), 7.2 (s, 1H, 7.7 (s, 1H), 8.5 (s, 1H).

EXAMPLE 26

Other trans-6-Substituted-7- or 8-substituted-3-[3-(3-methoxypiperid-2-yl)-2-oxopropyl]-quinazolin-4(3H)-one Dihydrobromides By the method of Example 5, other products of Example 19 were converted to the instant title products substituted as follows:

| 6-Substituent | 7- or 8-Substituent | Yield | m.p.(°C.) |
|---|---|---|---|
| methylthio | none | 43 | 223–225 |
| ethylthio | none | 39 | 203–205 |
| propylthio | none | 40 | (a) |
| 4-bromobenzylthio | none | 38 | 194–196 |
| methylthio | 7-chloro | 43 | 234–236 |
| ethylthio | 7-chloro | 34 | 219–222 |
| propylthio | 7-chloro | 59 | 212–214 |
| methylthio | 8-bromo | 60 | 210–214 |
| ethylthio | 8-chloro | 29 | 211–213 |
| ethylthio | 8-bromo | 48 | 188–192 |
| chloro | 7-methylthio | 41 | 225–255 |
| chloro | 8-methylthio | 64 | 250–253 |

[a] $^1$H-NMR(CF$_3$CO$_2$H) 1.2 (t, 3 H), 1.4–2.4 (m, 6 H), 3.2 (t, 2 H), 3.6 (s, 3 H), 5.6 (s, 2 H), 7.8–8.4 (m, 4 H).

EXAMPLE 27

Other trans-6-Substituted-7- or 8-substituted-3-[3-(3-hydroxypiperid-2-yl)-2-oxopropyl]-quinazolin-4(3H)-one Dihydrobromides By the method of Example 6, the products of the preceeding Example are converted to title products substituted as follows:

| 6-Substituent | 7- or 8-Substituent | Yield | m.p.(°C.) |
|---|---|---|---|
| methylthio | none | 90 | foam[a] |
| ethylthio | none | 69 | 193–195 |
| propylthio | none | 49 | 203–205 |
| 4-bromobenzylthio | none | 45 | 158–160 |
| methylthio | 7-chloro | 78 | 233–234 |
| ethylthio | 7-chloro | 45 | 233–234 |
| propylthio | 7-chloro | 70 | 220–221 |
| methylthio | 8-bromo | 82 | 224–226 |
| ethylthio | 8-chloro | 84 | 228–229 |
| ethylthio | 8-bromo | 59 | 212–214 |
| chloro | 7-methylthio | 35 | 250–256 |
| chloro | 8-methylthio | 76 | 228–230 |

[a] $^{13}$C-NMR(DMSO-d$_6$) 14.885, 20.226, 30.766, 39.600, 43.160, 54.657, 56.410, 66.718, 121.074, 121.365, 126.453, 132.807, 138.681, 147.513, 158.840, 200.193.

EXAMPLE 28

Methyl trans-2-[3-(6-Trifluoromethylquinazolin-4(3H)-on-3-yl)-2-oxopropyl]-3-methoxypiperidine-1-carboxylate By the method of Example 4, 6-trifluoromethylquinazolin-4(3H)-one and methyl trans-2-(3-bromo-2-oxopropyl)-3-methoxypiperidine-1-carboxylate were converted into the title compound in 24% yield; m.p. 137°–140° C. $^1$H—NMR(CDCl$_3$) 1.4–1.9 (m, 4H), 2.9 (d, 2H), 3.3 (s, 3H), 3.5–3.9 (m, 4H), 3.7 (s, 3H), 5.2 (s, 2H), 7.7–8.7 (m, 4H).

EXAMPLE 29

Methyl trans-2-[3-(6-Trifluoromethylquinazolin-4(3H)-on-3-yl)-2-oxopropyl]-3-hydroxypiperidine-1-carboxylate A 35 ml single neck round bottom flask equipped with a magnetic stirring bar was flame dried and then stoppered with a serum cap. Through a syringe needle the flask was evacuated and filled with dry nitrogen four times. A solution of 0.35 g (0.0008 mol) of title product of the preceding Example and 10 ml of dichloromethane was injected into the reaction flask, and with stirring the temperature was lowered to −70° C. Again with a syringe 3.0 ml of 1.0M boron tribromide in dichloromethane was introduced into the reaction vessel. After 10 minutes the reaction temperature was allowed to rise to −10° C. and was held there for 150 minutes. The reaction mixture was then combined with 11 ml of saturated sodium bicarbonate. The aqueous phase was separated and extracted three times with 5 ml portions of dichloromethane. The extracts were combined with the original organic layer, dried over anhydrous magnesium sulfate, and evaporated under reduced pressure to furnish the present title compound: yield 0.34 g, 100%; $^1$H—NMR(CDCl$_3$) 1.4–1.9 (m, 4H), 2.9 (d, 2H), 3.5–3.9 (m, 4H), 3.7 (s, 3H), 5.2 (s, 2H), 7.7–8.7 (m, 4H).

EXAMPLE 30 trans-6-Trifluoromethyl-3-[3-(3-hydroxypiperid-2-yl)-2-oxopropyl]quinazolin-4(3H)-one Dihydrobromide In a 15 ml single-neck round bottom flask equipped with a reflux condenser, a solution of 0.27 g (0.0006 mol) of title product of the preceding Example and 7 ml of 48% aqueous hydrobromic acid was immersed in an oil bath pre-heated to 150° C. Heating was continued for three minutes. The solution was allowed to cool to room temperature, and the volatile components were evaporated under reduced pressure. Ethanol (5 ml) was added to the residue, and again the mixture was evaporated to dryness. This operation was repeated once more to afford a dark residue which was then taken up in 3 ml of ethanol, heated at reflux briefly, and cooled to precipitate title product, 0.13 g (39%), m.p. 185°–190° C.

EXAMPLE 31

Allyl trans-2-[3-(6-Cyanoquinazolin-4(3H)-on-3-yl)-2-oxopropyl]-3-methoxypiperidine-1-carboxylate By the method of Example 4, 6-cyanoquinazolin-4(3H)-one and allyl trans-2-(3-bromo-2-oxopropyl)-3-methoxypiperidine-1-carboxylate were converted to title compound in 49% yield; $^1$H—NMR(CDCl$_3$) 1.2–1.9 (m, 4H), 2.9 (d, 2H), 2.9–3.5 (m, 4H), 4.6–6.2 (m, 5H), 5.2 (s, 2H), 7.8–8.6 (m, 4H).

EXAMPLE 32

Allyl trans-2-[3-(6-Cyanoquinazolin-4(3H)-on-3-yl)-2-oxopropyl]-3-hydroxypiperidine-1-carboxylate By the method of Example 20, title product of the preceding Example was converted to instant title product in 94% yield; $^1$H—NMR(DMSO-d$_6$) 1.2–1.9 (m, 4H), 2.9–3.8 (m, 6H), 4.5–6.2 (m, 5H), 5.1 (s, 2H), 7.8–8.6 (m, 4H).

EXAMPLE 33 trans-6-Cyano-3-[3-(3-acetoxypiperid-2-yl)-2-oxopropyl]quinazolin-4(3H)-one Dihydrobromide 1.34 g (0.0032 mol) of title product of the preceding Example was dissolved in 50 ml of 33% hydrobromic acid in glacial acetic acid at 0° C. and stirred for 30 minutes. The reaction mixture was poured into 750 ml of ether, and the resulting precipitate triturated several additional times with ether, and once with cold acetonitrile to give 880 mg of crude product, m.p. 226°–228°. This was recrystallized from ethanol to afford 535 mg (32%) of the title compound, m.p. 227°–229° C.

EXAMPLE 34 trans-6-Cyano-3-[3-(3-hydroxypiperid-2-yl)-2-oxo-propyl]quinazolin-4(3H)-one Dihydrochloride Title product of the preceding Example, 0.25 g (0.00047 mol) was dissolved in 10.0 ml of 6N hydrochloric acid and allowed to stir at room temperature for 5 hours or until starting material is no longer detected by thin layer chromatography. The solvent was then removed at 26°–28° C. under vacuum and the resulting crude solid triturated with acetone to give 179 mg (96%) of the title compound, m.p. 229°–230° C.

Analysis calculated for $C_{17}H_{18}N_4O_3 \cdot 2HCl \cdot 1.5H_2O$: C, 47.90; H, 5.44; N, 13.14%. Found: C, 48.00; H, 5.15; N, 12.87%.

PREPARATION 1

4-Chloro-5-(4-chlorophenoxy)-2-nitrobenzoic Acid

To 30 ml of dry diglyme under a nitrogen atmosphere was added 0.960 g (0.02 mol) of sodium hydride dispersion in mineral oil (50%). The solution was cooled to 10° C. and 1.28 g (0.01M) 4-chlorophenol in 15 ml of dry diglyme was added dropwise while maintaining the temperature at 10° C. This was followed by the dropwise addition of 2.36 g (0.01 mol) of 4,5-dichloro-2-nitrobenzoic acid in 15 ml of dry diglyme. The reaction mixture was then heated to 153° C. (oil bath) for 1 hour and 45 minutes. The reaction mixture was cooled to room temperature and poured into an ice/water mixture. The pH was then adjusted to 1.5 with 6N hydrochloric acid. The solution was extracted with ethyl acetate, and the organic layer dried over anhydrous magnesium sulfate. The solvent was removed and the crude solid triturated with hexane, followed by recrystallization from carbon tetrachloride to give the title compound: yield 1.65 g (50%) m.p. 160°–162° C.

By the same method, the following other 2-nitrobenzoic acids were prepared from the appropriate $Y^1$ substituted phenol and 5-$X^1$ substituted 2-nitrobenzoic

| $Y^1$ | $X^1$ | m.p.(°C.) | Yield(%) |
|---|---|---|---|
| H | H | 149–152 | 58 |
| 4-Br | H | 153–156 | 40 |
| 4-Cl | H | 140–148 | 40 |
| 3-Cl | H | 160–161 | 31 |
| 2-Cl | H | 105–115 | 50 |
| 3,5-diCl | H | 195–197 | 37 |
| 4-OPh | H | 132–134 | 57 |
| 4-Br | Cl | 208–210 | 76 |
| 4-Cl | Cl | 160–162 | 50 |
| 4-F | F | 178–181 | 50 |
| 4-Cl | Br | 147–150 | 38 |
| 3-Cl | Cl | 167–169 | 50 |
| 3-Br | Cl | 168–170 | 44 |

PREPARATION 2

2-Amino-4-chloro-5-(4-chlorophenoxy)benzoic Acid

A solution of title product of the preceding Preparation (4.14 g, 0.013 mol) in 100 ml of ethanol was hydrogenated at 50 psig over Raney nickel (4.14 g, water moist). After one hour, the reaction mixture was filtered and the mother liquor evaporated under reduced pressure to give 3.37 g (90%) of the title compound, m.p. 160°–170° C. This material was used in subsequent reactions without further purification.

By the same method, the other 2-nitrobenzoic acid derivatives of the preceding Preparation were converted to 2-amino-4-($X^1$ substituted)-5-($Y^1$ substituted phenoxy)-benzoic acids as follows:

| $Y^1$ | $X^1$ | m.p.(°C.) | Yield(%) |
|---|---|---|---|
| H | H | 142–144 | 83 |
| 4-Br | H | 159–160 | 44 |
| 4-Cl | H | 138–148 | 85 |
| 3-Cl | H | 146–150 | 80 |
| 2-Cl | H | foam* | 86 |
| 3,5-diCl | H | 180–187 | 73 |
| 4-OPh | H | 132–134 | 81 |
| 4-Br | Cl | 208–210 | 76 |
| 4-F | Cl | 192–193 | 79 |
| 4-Cl | Br | 194–196 | 93 |
| 3-Cl | Cl | 174–176 | 56 |
| 3-Br | Cl | 177–180 | 81 |

*$^1$H-NMR(DMSO-$d_6$) shows multiplet at 6.7–7.8 ppm.

PREPARATION 3

7-Chloro-6-(4-chlorophenoxy)quinazolin-4-(3H)-one

[Formula (VI) with $X^1$=7-chloro and $R^1$=4-chlorophenoxy]

A suspension of 3.3 g (0.011 mol) of title product of the preceding Preparation and 3.04 g (0.068 mol) of formamide was heated at 155° C. (oil bath). Within ten minutes the solid went into solution. After a total reaction time of 2 hours and 30 minutes, the solution was cooled and poured into water. The crude product was filtered and recrystallized from isopropyl alcohol. Yield 1.91 g (56%); m.p. 250°–252° C.

By the same method other products of the preceding Preparation were converted to 7-($X^1$ substituted)-6-($Y^1$ substituted phenoxy)quinazolin-4(3H)-ones [of the formula (VI)] as follows:

| $Y^1$ | $X^1$ | m.p.(°C.) | Yield(%) |
|---|---|---|---|
| H | H | 196–199 | 83 |
| 4-Br | H | 219–222 | 62 |
| 4-Cl | H | 207–211 | 83 |
| 3-Cl | H | 206–207 | 85 |
| 2-Cl | H | 190–193 | 66 |
| 3,5-diCl | H | 237–238 | 86 |
| 4-OPh | H | 196–197 | 36 |
| 4-Br | 7-Cl | 278–279 | 43 |
| 4-F | 7-Cl | 213–214 | 35 |
| 4-Cl | 7-Br | 267–269 | 62 |
| 3-Cl | 7-Cl | 266–267 | 43 |
| 3-Br | 7-Cl | 258–260 | 51 |

PREPARATION 4

5-Bromo-2-methylaniline

A suspension of 300 g (1.39 mol) of 4-bromo-2-nitrotoluene 370 g (9.25 mol) of sodium hydroxide, and 4 liters of water was treated with 400 g (3.7 mol) of formamidine sulfinic acid. The mixture was heated under reflux overnight, and then steam distilled. When 16 liters of distillate had been collected, the distillation was stopped. The distillate was separated into aqueous and organic layers. The aqueous layer was extracted with ethyl acetate three times. The extracts were combined with the organic layer, dried over anhydrous sodium sulfate, filtered, and evaporated under reduced pressure to furnish the product as an oil: b.p. 84° C. at 0.075 mmHg; yield 231.1 g (90%). This material has been prepared previously by reducing the nitro compound with iron [J. Frejka and F. Vymetal, Coll. Czech. Chem. Commun., 7, 436–443 (1935); C. A. 30, 1370 (1936)].

PREPARATION 5

N-(4-Bromo-2-methylphenyl)acetamide

With mechanical stirring and ice-bath cooling, a solution of 231 g (1.24 mol) of 5-bromo-2-methylaniline and 250 ml of diethyl ether was treated dropwise with 152.2 g (1.49 mol, 140 ml) of acetic anhydride at such a rate as to maintain the reaction temperature below 5° C. The product precipitated from the reaction mixture and was filtered to give colorless crystals: yield 215.2 g (76%); m.p. 160°–161° C. [lit. m.p. 165° C., Frejka and Vymetal, loc, cit.].

PREPARATION 6

2-Acetylamino-4-bromobenzoic Acid

With mechanical stirring, a suspension of 215 g (0.942 mol) of N-(4-bromo-2-methyl)acetamide in a solution of 310 g (1.257 mol) of magnesium sulfate heptahydrate, 447 g (2.83 mol) of potassium permanganate and 10 liters of water was heated under reflux for six hours during which time the mixture's color changed from clear purple to brownish-black. Heating was stopped and 50 ml of methanol was added. When at room temperature, the reaction mixture was treated with 250 g of diatomaceous earth and 100 g of activated carbon, and was filtered to give a clear colorless solution. The solution was adjusted to pH 4.4 by the addition of concentrated hydrochloric acid, and the product precipitated. After filtering and drying the crystals, there was obtained 171.3 g (70%) of 2-acetylamino-4-bromobenzoic acid: m.p. 224°–225° C. [lit. m.p. 220° C., Frejka and Vymetal, loc. cit.].

PREPARATION 7

Ethyl 2-Amino-4-bromobenzoate

A solution of 119 g (0.461 mol) of 2-acetylamino-4-bromobenzoic acid and 3 liters of absolute ethanol was cooled to 0° C. and was then saturated with a stream of dry hydrogen chloride gas. The solution was then heated under reflux for 24 hours. Upon cooling to room temperature, the solution was evaporated to about 750 ml and then poured into 2 liters of aqueous saturated sodium bicarbonate. The aqueous phase was extracted three times with 300 ml portions of chloroform. The combined extracts were dried over anhydrous sodium sulfate, filtered, and evaporated to afford 23.8 g (21%) of ethyl 2-amino-4-bromobenzoate as an oil: ir(CHCl$_3$) 3504 cm, 3390, 1685, 1610, 1580 among others; $^1$H—NMR(CDCl$_3$) 1.3 ppm triplet, 3H, CH$_2$CH$_3$), 4.3 (quartet, 2H, CH$_2$CH$_3$), 5.8 (broad singlet, 2H, NH$_2$), 6.6 [doublet (part of AB pattern), 1H, aromatic H], 6.8 (singlet, 1H, aromatic H), 7.7 [doublet (part of AB pattern), 1H, aromatic H].

PREPARATION 8

Ethyl 2-Amino-4-bromobenzoate Hydrochloride

At room temperature, a solution of 3.09 g (0.0127 mol) of ethyl 2-amino-4-bromobenzoate and 30 ml absolute ethanol was saturated with dry hydrogen chloride gas. A colorless precipitate formed in the warm solution. When it was again at room temperature, the solution was diluted with 30 ml of diethyl ether; the resulting crystalline product was filtered and washed with diethyl ether. Thus there was obtained 2.72 g (77%) of the title compound: m.p. 147°–150° C.

Analysis calculated for C$_9$H$_{11}$BrClNO$_2$: C, 38.53; H, 3.95; N, 4.99%. Found: C, 38.48; H, 4.02; N, 4.99%.

PREPARATION 9

Ethyl 2-Amino-4-bromo-5-thiocyanatobenzoate

In a 100 ml three-neck round bottom flask equipped with an internal thermometer and magnetic stirrer, a solution of 3.26 g (0.0116 mol) of ethyl 2-amino-4-bromobenzoate hydrochloride, 2.12 g (0.0279 mol) of ammonium thiocyanate and 30 ml of acetic acid was cooled to 15° C. Bromine (1.86 g, 0.0116 mol) was then added dropwise with stirring. A precipitate formed. When the addition was complete, the solution was allowed to warm to room temperature, and to stir for an hour. The product was filtered, dried under nitrogen, and recrystallized from hexane and ethyl acetate to furnish crystalline ethyl 2-amino-4-bromo-5-thiocyanatobenzoate: yield 2.05 g (59%); m.p. 149°–150° C.; ir(KBr) 3487 cm, 3453, 3375, 3346, 2980, 2146, 1697, 1614 among others; $^1$H—NMR(CDCl$_3$) 1.4 ppm (triplet, 3H, CH$_2$CH$_3$), 4.3 (quartet, 2H, CH$_2$CH$_3$), 6.0 (broad singlet), 6.9 (singlet, 1H, aromatic H), 8.1 (singlet, 1H aromatic H).

PREPARATION 10

Ethyl 2-Amino-4-bromo-5-methylthiobenzoate

Under a nitrogen atmosphere, with ice-bath cooling, and with magnetic stirring, 0.134 g (0.00585 mol) of sodium was dissolved in 20 ml of absolute ethanol. Ethyl 2-amino-4-bromo-5-thiocyanatobenzoate (0.88 g, 0.00292 mol) was added, and when solution was almost complete, the mixture was treated with 0.498 g (0.22 ml, 0.0035 mol) of methyl iodide. The solution was allowed to warm to room temperature, and to stir overnight. After pouring the reaction mixture into 200 ml of ice water, the resulting aqueous solution was adjusted to pH 6.5 by the addition of 2N hydrochloric acid. The aqueous solution was then extracted three times with 30 ml portions of ethyl acetate. The combined extracts were dried over anhydrous sodium sulfate, filtered, and evaporated to furnish the crude product: yield 0.88 g. This material was chromatographed under moderate pressure on a column of silica gel (i.d. 3.5 cm × height 17.5 cm); the eluant was 10% ethyl acetate/90% hexanes. Fractions of 20 ml each were collected. Fractions 27–38 gave crystals of the title compound: yield 0.66 g (78%); m.p. 48°–50° C.; ir(KBr) 3461 cm, 3354, 2976, 2914, 1680, 1603 among others; mass spectrum 289 (parent peak and molecular ion with expected isotope pattern), 274 (−15, —CH$_3$), 261 (−28, —CH$_2$CH$_2$), 243 (−46, —CH$_3$CH$_2$OH) among others; $^1$H—NMR(CDCl$_3$) 1.3 ppm (triplet, 3H, CH$_2$CH$_3$), 2.4 (singlet, 3H, SCH$_3$), 4.3 (quartet, 2H, CH$_2$CH$_3$), 5.8 (broad singlet, 2H, NH$_2$), 6.9 (singlet, 1H, aromatic H), 7.9 (singlet, 1H, aromatic H).

Analysis calculated for C$_{10}$H$_{12}$BrNO$_2$S: C, 41.39; H, 4.17; N, 4.83%. Found: C, 41.44; H, 4.14; N, 4.54%.

PREPARATION 11

7-Bromo-6-methylthioquinazolin-4(3H)-one Formic Acid Salt

In a flame dried 50 ml round bottom flask equipped with a magnetic stirrer and under a nitrogen atmosphere, a solution of 1.01 g (0.62 ml, 0.00659 mol) of phosphorous oxychloride and 5 ml of dry dimethylformamide was cooled to 0° C. In another 5 ml of dimethylformamide, 1.6 g (0.00552 mol) of ethyl 2-amino-4-bromo-5-methylthiobenzoate was added to the reaction flask. The solution was stirred for an hour at 0° C., and then 11 ml of concentrated ammonium hydroxide was added. The reaction mixture was allowed to come to room temperature, and was stirred overnight. After being poured into 30 ml of water, the reaction mixture was filtered, and the product was dried under nitrogen. It was then recrystallized from hot formic acid to furnish colorless crystals of the title compound: yield 1.33 g (76%); m.p. 272°–274° C.; mass spectrum 270 (parent peak and molecular ion with expected isotope pattern), 255 (−15, —CH$_3$) among others.

Analysis calculated for C$_{10}$H$_9$BrN$_2$O$_3$S: C, 37.87; H, 2.86; N, 8.83%. Found: C, 38.06; H, 2.97; N, 8.79%.

PREPARATION 12

Ethyl 2-Amino-4-bromo-5-ethylthiobenzoate

In the manner of Preparation 10, 2.5 g (0.0083 mol) of ethyl 2-amino-4-bromo-5-thiocyanatogbenzoate and 1.55 g (0.010 mol) of ethyl iodide were converted into the title compound: yield 1.78 g (70%); ir (neat) 3472 cm$^{-1}$, 3360, 2971, 2921, 2863, 1691, 1604, 1569, 1542 among others; mass spectrum peaks m/e 305 (parent peak, higher isotope), 303 (molecular ion) among others; $^1$H—NMR(CDCl$_3$) 1.4 ppm, ["quartet" (overlapping triplets, 6H, SCH$_2$CH$_3$, OCH$_2$CH$_3$], 2.3 (quartet, 2H, SCH$_2$CH$_3$), 4.4 (quartet, 2H, OCH$_2$CH$_3$), 5.9 (broad singlet, 2H, NH$_2$), 7.0 (singlet, 1H, aromatic H), 8.0 (singlet, 1H, aromatic H).

PREPARATION 13

7-Bromo-6-ethylthioquinazolin-4(3H)-one Formic Acid Salt

In the manner of Preparation 11, 1.78 g (0.00585 mol) of ethyl 2-amino-4-bromo-5-ethylthiobenzoate was transformed into the title compound: yield 1.22 g (63%); m.p. 272°–273° C.; mass spectrum m/e 286 (parent peak), 284 (molecular ion), 269 (−15, —CH$_3$), 256 (−28, —CO), 177 (−28, −79, —CO, —Br) among others.

Analysis calculated for C$_{11}$H$_{11}$BrN$_2$O$_3$S: C, 39.89; H, 3.35; Br, 24.13; N, 8.46; S, 9.68%. Found: C, 39.60; H, 3.20; Br, 25.40; N, 8.61; S, 9.94%.

PREPARATION 14

N-(4-Fluoro-2-methylphenyl)acetamide

In the manner of Preparation 5, 20 g (0.160 mol) of 5-fluoro-2-methylaniline was converted into the title compound: yield 25.0 g (94%); m.p. 131°–132° C., [lit. m.p. 133.5°–134° C.: E. A. Steck, L. T. Fletcher, J. Am. Chem. Soc. 70, 439–440 (1948)].

PREPARATION 15

2-Acetylamino-4-fluorobenzoic Acid

In the manner of Preparation 6, 12.5 g (0.075 mol) of N-(4-fluoro-2-methylphenyl)acetamide was transformed into the title compound: yield 11.88 g (81%); m.p. 212.5°–214.5° C., [lit. m.p. 209°–209.5° C.: Steck and Fletcher loc. cit.].

PREPARATION 16

Ethyl 2-Amino-4-fluorobenzoate

In the manner of Preparation 7, 30.79 g (0.156 mol) of 2-acetylamino-4-fluorobenzoic acid was converted into the title compound: yield 20.43 g (71%); ir (neat) 3482 cm, 3367, 2933, 2903, 2871, 1692, 1627, 1593, 1573, 1500; $^1$H—NMR(CDCl$_3$) 1.3 ppm (triplet, 3H, OCH$_2$CH$_3$), 4.3 (quartet, 2H, OCH$_2$CH$_3$), 5.8 (broad singlet, 2H, NH$_2$), 6.2–6.6 (multiplet, 2H, aromatic H), 7.2–8.0 (multiplet, 1H, aromatic H).

PREPARATION 17

Ethyl 2-Amino-4-fluorobenzoate Hydrochloride

In the manner of Preparation 8, 20.43 g (0.112 mol) of ethyl 2-amino-4-fluorobenzoate was transformed into its hydrochloride salt: yield 19.35 g (79%); licorice odor; m.p. 153°–156° C.; mass spectrum m/e 183 (molecular ion; 155 (−28, —CO), 138 (−45, —CH$_3$CH$_2$O), 137 (parent peak, −46, —CH$_3$CH$_2$OH), 110 (−73, —CO$_2$CH$_2$CH$_3$) among others; $^1$H—NMR(DMSO-d$_6$) 1.3 ppm (triplet, 3H, OCH$_2$CH$_3$), 4.2 (quartet, 2H, OCH$_2$CH$_3$), 6.3 (doublet of triplets, 1H, aromatic H), 6.6 (doublet of doublets, 1H, aromatic H), 7.8 (doublet of doublets, 1H, aromatic H), 8.2 (broad singlet, 2H, NH$_2$).

Analysis calculated for C$_9$H$_{11}$ClFNO$_2$: C, 49.21; H, 5.05; Cl, 16.14; F, 8.65; N, 6.38%. Found: C, 49.45; H, 4.89; Cl, 15.77; F, 8.63; N, 6.39%.

PREPARATION 18

Ethyl 2-Amino-4-fluoro-5-thiocyanatobenzoate

In the manner of Preparation 9, 15.22 g (0.0695 mol) of ethyl 2-amino-4-fluorobenzoate hydrochloride was used to prepare the title compound. The yield after "flash" chromatography (on silica gel; eluant hexanes:-chloroform 6:4) was 2.36 g (14%); m.p. 144°–145° C.; ir(KBr) cm$^{-1}$ 3453, 3341, 2979, 2932, 2899, 2141, 1698, 1625, 1591, 1552 among others; mass spectrum m/e 240 (molecular ion), 212 (−28, —CO), 194 (parent peak, −46, —CH$_3$CH$_2$OH) among others.

Analysis calculated for C$_{10}$H$_9$FN$_2$O$_2$S: C, 50.00; H, 3.75; N, 11.67; S, 13.33%. Found: C, 49.79; H, 3.78; N, 11.25; S, 13.09%.

PREPARATION 19

Ethyl 2-Amino-4-fluoro-5-methylthiobenzoate

In the manner of Preparation 10, 2.34 g (0.0097 mol) of ethyl 2-amino-4-fluoro-5-thiocyanatobenzoate was transformed into the title compound: yield 2.46 g (100%, some solvent included); ir(KBr) 3481 cm, 3367, 2980, 2917, 1688, 1620, 1582, 1556 among others; mass spectrum m/e 229 (molecular ion), 214 (−15, —CH$_3$), 201 (−28, —CO), 183 (parent peak, −46, —CH$_3$CH$_2$OH) among others; $^1$H—NMR(CDCl$_3$) 1.3 ppm (triplet, 3H, OCH$_2$CH$_3$), 2.3 (singlet, 3H, SCH$_3$), 4.2 (quartet, 2H, OCH$_2$CH$_3$), 6.0 (broad singlet, 2H, NH$_2$), 6.3 (doublet, 1H, aromatic H), 7.9 (doublet, 1H, aromatic H).

PREPARATION 20

7-Fluoro-6-methylthioquinazolin-4(3H)-one Formic Acid Salt

In the manner of Preparation 11, 2.46 g (0.0107 mol) of ethyl 2-amino-4-fluoro-5-methylthiobenzoate was converted into the title compound: yield 0.83 g (30%);

mass spectrum m/e 210 (molecular ion and parent peak), 195 (−15, —CH$_3$) among others; $^1$H—NMR(DMSO-d$_6$) 2.6 ppm (singlet, 3H, SCH$_3$), 7.4 (doublet, 1H, aromatic H), 7.9 (doublet, 1H, aromatic H), 8.0 (singlet, 1H, N=CH—N), 8.1 (singlet, 1H, HCO$_2$H).

Analysis calculated for C$_{10}$H$_9$FN$_2$O$_3$S: C, 46.87; H, 3.54; N, 10.93; S, 12.51%. Found: C, 47.58; H, 3.38; N, 11.45; S, 13.67%.

PREPARATION 21

N-(4-Iodo-2-methylphenyl)acetamide

In the manner of Preparation 5, 10 g (0.043 mol) of 5-iodo-2-methylaniline was converted into the title compound: yield 11.1 g (94%); m.p. 182°–183° C.

Analysis calculated for C$_9$H$_{10}$INO: C, 39.29; H, 3.66; N, 5.09%. Found: C, 39.61; H, 3.77; N, 4.96%.

PREPARATION 22

2-Acetylamino-4-iodobenzoic Acid

In the manner of Preparation 6, 10 g (0.036 mol) of N-(4iodo-2-methylphenyl)acetamide was transformed into the title compound: yield 4.66 g (42%); m.p. 229°–232° C.

Analysis calculated for C$_9$H$_8$INO$_3$: C, 35.43; H, 2.64; I, 41.60, N; 4.59%. Found: C, 35.28; H, 2.66; I, 41.19; N, 4.51%.

PREPARATION 23

Ethyl 2-Amino-4-iodobenzoate

In the manner of Preparation 7, 31.22 g (0.102 mol) of 2-acetylamino-4-iodobenzoic acid was converted into the title compound: yield 17.65 g (59%); m.p. 51°–53° C.; ir (neat) 3475 cm, 3363, 2974, 2927, 2896, 1689, 1603, 1578, 1543; mass spectrum m/e 291 (molecular ion and parent peak), 245 (−46, —CH$_3$CH$_2$OH) among others; $^1$H—NMR(CDCl$_3$) 1.3 ppm (triplet, 3H, OCH$_2$CH$_3$), 4.3 (quartet, 2H, OCH$_2$CH$_3$), 5.7 (broad singlet, 2H, NH$_2$), 6.9 (doublet, 1H, aromatic H), 7.0 (singlet, 1H, aromatic H), 7.5 (doublet, 1H, aromatic H).

Analysis calculated for C$_9$H$_{10}$INO$_2$: C, 37.13; H, 3.46; I, 43.60; N, 4.81%. Found: C, 36.83; H, 3.35; I, 43.12; N, 5.52%.

PREPARATION 24

Ethyl 2-Amino-4-iodobenzoate Hydrochloride

In the manner of Preparation 8, 18.75 g (0.0644 mol) of ethyl 2-amino-4-iodobenzoate was transformed into its hydrochloride salt: yield 19.20 g (91%); m.p. 147°–149° C.; mass spectrum m/e 291 (molecular ion and parent peak), 245 (−46, —CH$_3$CH$_2$OH) among others; $^1$N—NMR(DMSO-d$_6$) 1.3 ppm (triplet, 3H, OCH$_2$CH$_3$), 4.2 (quartet, 2H, OCH$_2$CH$_3$), 6.9 (doublet of doublets, 1H, aromatic H), 7.3 (doublet, 1H, aromatic H), 7.4 (doublet, 1H, aromatic H), 7.8 (broad singlet, 2H, NH$_2$).

Analysis calculated for C$_9$H$_{11}$ClINO$_2$: C, 33.00; H, 3.39; I, 38.74; N, 4.28%. Found: C, 33.01; H, 3.36; I, 37.36; N, 4.24%.

PREPARATION 25

Ethyl 2-Amino-4-iodo-5-thiocyanatobenzoate

In the manner of Preparation 9, 17.05 g (0.052 mol) of ethyl 2-amino-4-iodobenzoate hydrochloride was used to prepare the title compound. The yield after flash chromatography (on silica gel; eluant hexanes: chloroform 6:4) was 10.3 g (57%): m.p. 164°–165.5° C.; ir(KBr) cm$^{-1}$ 3449, 3345, 2966, 2920, 2142, 1693, 1613, 1566, 1534 among others; mass spectrum m/e 348 (molecular ion and parent peak), 320 (−28, —CO), 302 (−46, —CH$_3$CH$_2$OH) among others; $^1$H—NMR(CDCl$_3$) 1.3 ppm (triplet, 3H, OCH$_2$CH$_3$), 4.2 (quartet, 2H, OCH$_2$CH$_3$), 5.8 (broad singlet, 2H, NH$_2$), 7.2 (singlet, 1H, aromatic H), 8.2 (singlet, 1H, aromatic H).

Analysis calculated for C$_{10}$H$_9$IN$_2$O$_2$S: C, 34.50; H, 2.61; I, 36.45; N, 8.05; S, 9.21%. Found: C, 33.94; H, 2.54; I, 35.20; N, 7.74; S, 10.54%.

PREPARATION 26

Ethyl 2-Amino-4-iodo-5-(methylthio)benzoate

In the manner of Preparation 10, 3.0 g (0.0086 mol) of ethyl 2-amino-4-iodo-5-thiocyanatobenzoate was transformed into the title compound: yield 1.79 g (62%); m.p. 59°–60° C.; ir(KBr) 3414 cm, 3311, 2980, 2906, 1690, 1607, 1568, 1549 among others; mass spectrum m/e 337 (molecular ion and parent peak), 322 (−15, —CH$_3$), 309 (−28, —CO), 291 (−46, —CH$_3$CH$_2$OH) among others; $^1$H—NMR (CDCl$_3$) 1.4 ppm (triplet, 3H, OCH$_2$CH$_3$), 2.4 (singlet, 3H, SCH$_3$), 4.3 (quartet, 2H, OCH$_2$CH$_3$), 5.7 (broad singlet, 2H, NH$_2$), 7.2 (singlet, 1H, aromatic H), 7.8 (singlet, 1H, aromatic H).

Analysis calculated for C$_{10}$H$_{12}$INO$_2$S: C, 35.61; H, 3.56; N, 4.15%. Found: C, 35.80; H, 3.63; N, 4.08%.

PREPARATION 27

7-Iodo-6-methylthioquinazolin-4(3H)-one Formic Acid Salt

In the manner of Preparation 11, 2.5 g (0.0074 mol) of ethyl 2-amino-4-iodo-5-methylthiobenzoate was converted into the title compound: yield 1.23 g (46%); m.p. 268°–270° C.; mass spectrum m/e 318 (molecular ion and parent peak) among others; $^1$H—NMR(DMSO-d$_6$) 2.6 ppm (singlet, 3H, SCH$_3$), 7.6 (singlet, 1H, aromatic H), 8.0 (singlet, 1H, aromatic H), 8.05 (singlet, 1H, N=CH—N), 8.1 (singlet, 1H, HCO$_2$H).

Analysis calculated for C$_{10}$H$_9$IN$_2$O$_3$S: C, 32.97; H, 2.47; N, 7.69%. Found: C, 33.14; H, 2.68; N, 7.81%.

PREPARATION 28

6-Chloro-7-methylthioquinazolin-4(3H)-one

Under a nitrogen atmosphere in a flame dried flask equipped with a magnetic stirrer and a reflux condenser, a mixture of 1.00 g (0.00465 mol) of 6,7-dichloroquinazolin-4(3H)-one and 18 ml of dimethylformamide was treated at room temperature with 0.56 g (0.012 mol) of 50% sodium hydride in mineral oil. Foaming began immediately and most of the solids dissolved. When the foaming had subsided, 1.8 ml (0.0176 mol) of 47% methyl mercaptan in dimethyl formamide was added to the stirred mixture. The mixture was heated at 120° C. for six hours. When the reaction mixture was again at room temperature, a small amount of insoluble matter was filtered, and was rinsed with a few ml of dimethylformamide. The filtrate was washed three times with 10 ml portions of hexane. The filtrate was then poured into 300 ml of ice and water. By the addition of 2N hydrochloric acid, the aqueous solution was adjusted to pH 2. There formed a fine colorless precipitate which was filtered, washed with water, air dried and pressed on a clay plate to furnish the title compound: yield 0.97 g (92%); m.p. 292°–295° C. (dec.); mass spectrum m/e 226 (parent peak and molecular ion with expected isotope pattern), 193 (−33) among others; $^1$H—NMR(DMSO-d$_6$) 2.6 ppm (singlet, 3H, SCH$_3$), 7.45 (singlet, 1H, aromatic H), 8.0 (singlet, 1H, aromatic H), 8.15 (singlet, 1H, N=CH—N).

PREPARATION 29

2-Amino-5-(ethylthio)benzoic Acid

To a 500 ml flask fitted with a magnetic stirrer, dropping funnel and thermometer, and containing a solution of 12.7 g (0.192 mol) of 85% potassium hydroxide in 300 ml of methanol was added in portions 10.0 g (0.0481 mol) of methyl 2-amino-5-thiocyanatobenzoate. The solution was cooled to 10° C. and a solution of 6.29 g (0.058 mol) ethylbromide in 50 ml of methanol was added over 10 minutes. This was followed by the addition of 8.0 g (0.048 mol) potassium iodide. After 2.5 hours, the reaction mixture was evaporated to a semi-solid under reduced pressure and treated with 300 ml of water. The aqueous solution was extracted with chloroform, and the organic layer dried over magnesium sulfate. The solution was filtered and evaporated to give 7.5 g (79%) of crude product. This material was recrystallized from hexane to give 3.01 g (32%) of the title compound, m.p. 97°–100° C.

PREPARATION 30

2-Amino-5-(propylthio)benzoic Acid

To a solution containing 50 ml of water, 25 ml of methanol and 6 ml of 1N sodium hydroxide was added 0.88 g (0.0037 mol) of ethyl 2-amino-5-propylthiobenzoate. The reaction was heated at reflux for 1 hour, cooled to room temperature, concentrated to a white solid and treated with 200 ml of water. The solution was then acidified with 6N hydrochloric acid and the resulting white precipitate filtered and dried to afford 0.54 g (70%) of the title compound, m.p. 91°–93° C.

PREPARATION 31

2-Amino-5-(methylthio)benzoic Acid

By the method of Preparation 2, 2-nitro-5-(methylthio)benzoic acid [Tilley et al., Org. Prep. Proced. 13, pp 189–196 (1984)] was converted to instant title product in 70% yield, m.p. 148°–150° C.

PREPARATION 32

Other Thiocyanato-2-aminobenzoate Esters

By the method of Preparations 9, 18 and 25, ethyl 2-aminobenzoate and appropriately 3- or 4-substituted ethyl 2-aminobenzoates were converted to the following ethyl 2-amino-5-thiocyanatobenzoates:

| Further Substituents | Yield | m.p.(°C.) |
| --- | --- | --- |
| None | 44 | 104–106 |
| 4-chloro | 45 | 151–153 |
| 3-chloro | 69 | 76–78 |
| 3-bromo | 63 | 63–65.5 |
| 4-methoxy | 63 | 106–108 |

By the same method, methyl 2-aminobenzoate was converted to methyl 2-amino-5-thiocyanatobenzoate (m.p. 110°–112° C.) in 69% yield.

By the same method, ethyl 2-amino-5-chlorobenzoate was converted to ethyl 2-amino-5-chloro-3-thiocyanatobenzoate (m.p. 128°–130° C.) in 8% yield.

PREPARATION 33

Other Alkylthio-2-aminobenzoate Esters and Related Compounds

By the method of Preparations 10, 19 and 26, substituting an equivalent amount of the appropriate alkyl, benzyl or picolyl halide for methyl iodide, the following ethyl 5-substituted-3- or 4-substituted-2-aminobenzoates were prepared from the products of the preceding Example:

| Substituents | Yield | m.p.(°C.) |
| --- | --- | --- |
| 5-methylthio | 82 | 34–36 |
| 5-ethylthio | 84 | 51–53 |
| 5-propylthio | 83 | oil$^{(a)}$ |
| 5-(4-bromobenzylthio) | 68 | oil$^{(b)}$ |
| 5-(4-chlorobenzylthio)-4-chloro | 52 | 82–85 |
| 5-(4-bromobenzylthio)-4-chloro | 100 | 72–81 |
| 5-(4-picolylthio)-4-chloro | 93 | 102–107 |
| 5-methylthio-4-methoxy | 61 | 92–94 |
| 5-methylthio-4-chloro | 82 | 50.5–53.5 |
| 5-ethylthio-4-chloro | 100 | oil$^{(c)}$ |
| 5-propylthio-4-chloro | 99 | oil$^{(d)}$ |
| 5-ethylthio-4-bromo | 70 | oil$^{(e)}$ |
| 5-methylthio-3-chloro | 100 | oil$^{(f)}$ |
| 5-methylthio-3-bromo | 77 | oil$^{(g)}$ |
| 5-ethylthio-3-chloro | (h) | — |
| 5-ethylthio-3-bromo | 91 | oil$^{(i)}$ |
| 3-methylthio-5-chloro | 20 | oil$^{(j)}$ |

$^{(a)}$m/e 239.0980 (molecular ion).
$^{(b)}$H-NMR(CDCl$_3$) 1.3 (t, 3 H), 3.8 (s, 2 H), 4.2 (q, 2 H), 6.4 (d, 1 H), 7.1 (m, 5 H), 7.7 (d, 1 H).
$^{(c)}$m/e 259/261 (chlorine isotope).
$^{(d)}$H-NMR(CDCl$_3$) 1.4 (m, 8 H), 2.8 (t, 2 H), 4.2 (q, 2 H), 6.5 (s, 1 H), 8.0 (s, 1 H).
$^{(e)}$m/e 303/305 (molecular ion, chlorine isotope).
$^{(f)}$m/e 245/247 (molecular ion, chlorine isotope).
$^{(g)}$m/e 289/291 (molecular ion, bromine isotope).
$^{(h)}$hydrolyzed in next step without characterization; over-all yield 35%.
$^{(i)}$correctly analyses for C$_{11}$H$_{14}$O$_2$NSBr.
$^{(j)}$m/e 245.0366 (molecular ion).

PREPARATION 34

Other Alkylthio-2-aminobenzoic Acids

By the method of Preparation 30, appropriate products of the preceding Example were hydrolyzed to yield the following 3-substituted-5-substituted-2-aminobenzoic acids:

| 3-Substituent | 5-Substituent | Yield | m.p.(°C.) |
| --- | --- | --- | --- |
| chloro | methylthio | 57 | 157–162 |
| bromo | methylthio | 75 | 159–162 |
| chloro | ethylthio | 35$^{(a)}$ | 133–135 |
| bromo | ethylthio | 77 | 121.5–123.5 |
| methylthio | chloro | 80 | 156–159 |

$^{(a)}$yield over 2-steps

PREPARATION 35

Other Alkylthioquinazolin-4(3H)-ones

By the method of Preparation 3, 2-aminobenzoic acids of preceding Preparations 30, 31 and 35 were converted to the following substituted quinazolin-4(3H)-ones:

| Substituents | Yield | m.p.(°C.) |
| --- | --- | --- |
| 6-methylthio | 72 | 200–202 |
| 6-ethylthio | 66 | 166–169 |
| 6-propylthio | 62 | 151–154 |
| 6-methylthio-8-chloro | 63 | 257–263 |
| 6-methylthio-8-bromo | 65 | 275–280 |
| 6-ethylthio-8-chloro | 77 | 267–270 |

| -continued | | |
|---|---|---|
| Substituents | Yield | m.p.(°C.) |
| 6-chloro-8-methylthio | 59 | 324–327 |

PREPARATION 36

Other Substituted Quinazolin-4(3H)-ones Formic Acid Salts

By the method of Preparations 11, 13, 20 and 27, appropriately substituted ethyl 2-aminobenzoates of Preparation 34 were converted to the following substituted quinazolin-4(3H)-ones:

| Substituents | Yield | m.p.(°C.) |
|---|---|---|
| 6-(4-bromobenzylthio) | 74 | 209–212 |
| 6-(4-chlorobenzylthio)-7-chloro | 69 | 245–248 |
| 6-(4-bromobenzylthio)-7-bromo | 51 | 265–268 |
| 6-(4-picolylthio)-7-chloro | 45 | 196–207 |
| 6-methylthio-7-methoxy | 50 | 292–294 |
| 6-methylthio-7-chloro | 58 | 270–274 |
| 6-ethylthio-7-chloro | 54 | 238–241 |
| 6-propylthio-7-chloro | 48 | 202–205 |

PREPARATION 37

4-Trifluoromethyl-N-pivaloylaniline

To a solution of 6.87 g (0.043 mol) of 4-trifluoromethylaniline in 110 ml of dichloromethane was added 5.25 ml (0.043 mol) of pivaloylchloride. After stirring for 1.5 hours, 190 ml of a saturated solution of aqueous sodium bicarbonate was added. The reaction proceeded an additional 2 hours and the organic layer was separated and dried over anhydrous magnesium sulfate. The solution was filtered and the solvent removed to give the title compound, yield 9.16 g (88%), m.p. 154°–158° C.

PREPARATION 38

2-(N-Pivaloyl)-5-trifluoromethylbenzoic Acid

A solution of 25.0 g (0.102 mol) of 4-trifluoromethyl-N-pivaloylaniline in 140 ml of dry tetrahydrofuran was cooled to 5° C. under a nitrogen atmosphere. This was followed by the dropwise addition of 110 ml (0.22 mol) of 2.0M n-butyllithium in hexane. The addition was carried out over 2 hours while maintaining the temperature below 15° C. When the addition was complete, the temperature was raised to 20° C. and the reaction stirred for 7 hours. The solution was then cooled to −60° C. and dry carbon dioxide gas was bubbled through the reaction at a rapid rate for 15 minutes, during which time the thick suspension was diluted with an additional 150 ml of dry tetrahydrofuran. After stirring for 16 hours, the reaction mixture was treated with 100 ml of saturated aqueous ammonium chloride. The reaction mixture was then concentrated to 150 ml and diluted with 1.0 liter of water. The pH was adjusted to 1.0 with hydrochloric acid, and the resulting solution extracted with ethyl acetate. The organic layer was dried over magnesium sulfate, filtered and evaporated under reduced pressure to afford the crude product. This was recrystallized from toluene to give 7.8 g (26%) of the title compound, m.p. 196°–198° C.

PREPARATION 39

Methyl 2-Amino-5-trifluoromethylbenzoate

A solution of 7.46 g (0.026 mol) of 2-(N-pivaloyl)-5-trifluoromethylbenzoic acid in 300 ml of methanol was cooled to 5° C. and saturated with gaseous hydrochloric acid. The reaction mixture was then heated at reflux for 20 hours, and evaporated to a solid. The crude solid was dissolved in chloroform and washed with saturated aqueous sodium bicarbonate. The organic layer was dried and evaporated to a viscous oil, which was purified by silica gel chromatography (9:1 hexane:ethylacetate). The title compound was isolated as a white solid, m.p. 51°–52° C.; yield 4.0 g (71%).

PREPARATION 40

6-Trifluoromethylquinazolin-4(3H)-one

By the method of Preparation 11, title product of the preceding Preparation was converted to instant title product in 71% yield, m.p. 209°–211° C.

Analysis calculated for $C_9H_5N_2OF_3$: C, 50.47; H, 2.34; N, 13.08%. Found: C, 49.81; H, 2.28; N, 12.98%.

PREPARATION 41

6-Cyanoquinazolin-4(3H)-one

6-Aminoquinazolin-4(3H)-one was slurried in 300 ml of 5% hydrochloric acid and the reaction mixture was cooled to 5° C. A solution of 6.72 g (0.097 mol) of sodium nitrite in 30 ml of water was added dropwise over 2.5 hours while maintaining the reaction temperature below 10° C. The resulting diazonium salt was then added portionwise to a hot (86° C.) solution of 7.84 g (0.0876 mol) of copper cyanide and 11.0 g (0.224 mol) sodium cyanide in 60 ml of water. Evolution of nitrogen was evident throughout the addition. After stirring for 30 minutes, the reaction mixture was filtered, washed with water, and air-dried. The crude product (9.1 g) was purified by silica gel chromatography to afford 3.89 g (26%) of the title compound; m.p. 294°–300° C.

I claim:

1. A compound having the formula

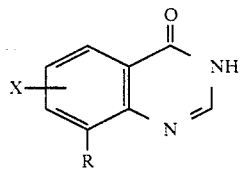

(V)

or

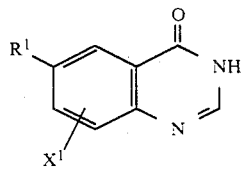

(VI)

wherein

X is fluoro, chloro, bromo or iodo substituted at the 6- or 7-position;

R is $(C_1-C_4)$alkylthio;

$X^1$ is hydrogen or fluoro, chloro, bromo, iodo or methoxy substituted either at the 7- or at the 8-position;

$R^1$ is cyano, trifluoromethyl, $(C_1-C_4)$alkylthio 4-picolylthio, 3,5-dichlorophenoxy,
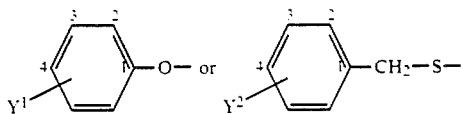
where $Y^1$ is hydrogen, fluoro, chloro, bromo or phenoxy; and $Y^2$ is chloro or bromo; with the proviso that $Y^1$ is other than hydrogen when $X^1$ is other than hydrogen.
* * * * *